(12) United States Patent
Kimura

(10) Patent No.: US 6,564,080 B1
(45) Date of Patent: May 13, 2003

(54) MR IMAGING ON ASL TECHNIQUE

(75) Inventor: Tokunori Kimura, Yaita (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 0 days.

(21) Appl. No.: 09/539,775

(22) Filed: Mar. 31, 2000

(30) Foreign Application Priority Data

Mar. 31, 1999 (JP) .......................................... 11-090918

(51) Int. Cl.$^7$ ................................................ A61B 5/05
(52) U.S. Cl. ........................ 600/410; 324/307; 324/309
(58) Field of Search ................................ 324/307, 309; 128/653.3; 600/407, 410

(56) References Cited

U.S. PATENT DOCUMENTS

| | | | | |
|---|---|---|---|---|
| 5,320,099 A | * | 6/1994 | Roberts et al. | 128/653.3 |
| 5,627,468 A | * | 5/1997 | Kojima et al. | 324/307 |
| 5,846,197 A | * | 12/1998 | Edelman | 600/419 |
| 6,271,665 B1 | * | 8/2001 | Berr et al. | 324/306 |

OTHER PUBLICATIONS

R. R. Edelman et al., "Qualitatve Mapping of Cerebral Blood Flow and Functional Localization with Echoplanar MR imaging and Signal Targeting with Alternating Radio Frequency", Radiology 1994; 192:513–520.

A. Haase, "Snapshot Flash MRI. Applications to T1, T2, and Chemical–Shift Imaging", Magnetic Resonance In Medicine 13, 77–89 (1990).

K. K. Kwong et al., "MR Perfusion Studies with T1–Weighted Echo Planar Imaging", MRM 34 878–887 (1995).

V. M. Mai et al., "Alternative of Selective Inversion Pulses (ASI): An MR Perfusion Imaging Technique with Shorter Transit Time of Labeled Blood Than Signal Targeting Alternating Radiofrequency (STAR)", ISMRM 1998.

R. R. Edelman et al., "Epistar MRI" Multislice Mapping of Cerebral Blood Flow, MRM 40:800–805 (1998).

A. C. Silva et al., "Multi–Slice MRI of Rat Brain Perfusion During Amphetamine Stimulation Using Arterial Spin Labeling", MRM 33: 209–214 (1995).

[lsp10]D. C. Alsop et al., "Multisection Cerebral Blood Flow MR Imaging with Continuous Arterial Spin Labeling", Radiology 1998: 208: 410–416.

[lsp11]S. Mani et al., "Background Suppression with Multiple Inversion Recovery Nulling: Applications to Projective Angiography", MRM 37: 898–905 (1997).

* cited by examiner

Primary Examiner—Marvin M. Lateef
Assistant Examiner—Devaang Shah
(74) Attorney, Agent, or Firm—Nixon & Vanderhye P.C.

(57) ABSTRACT

MR imaging is provided based on the ASL method providing an ASL image. In this imaging, MT effects are steadily canceled to reduce difference errors inherent in excluding stationary tissue from the image and sensitivity is given to only a signal from one-way blood flow. A first RF wave and a first magnetic gradient $G_{tag}$ both for selective-exciting a tagging slab and a second RF wave and a second magnetic gradient $G_{cont}$ both for selective-exciting a controlling slab are set, in which offset amounts of exciting central frequencies of both of the first and second RF waves to a central position of an imaging slab are equal to each other and offset positions Offset$_{tag}$ and Offset$_{cont}$ of the tagging slab and the controlling slab to the imaging slab are different from each other. Both of the RF pulses are IR pulses. A pulse sequence including the first RF wave and the first magnetic gradient $G_{tag}$ is performed and a pulse sequence including the second RF wave and the second magnetic gradient $G_{cont}$ is performed, so that echo signals are acquired for each performance. The echo signals are subject to mutual difference calculation to provide an ASL image.

22 Claims, 23 Drawing Sheets

Relationship between Control-IR
and Tag-IR slabs in ASTAR (PASL)

Relationship between Control-IR
and Tag-IR slabs in ASTAR (PASL)

Relationship between Control-IR and Tag-IR slabs in EPISTAR

Relationship between Control-IR
and Tag-IR slabs in ASTAR (DASL)

MR IMAGING ON ASL TECHNIQUE

BACKGROUND OF THE INVENTION

The present invention is related to an MRI (magnetic resonance imaging) system and an MR imaging method both of which make use of the magnetic resonance phenomenon of nuclear spins present in a subject's body, in particular, to the MRI system and the MR imaging method for conducting an ASL (Arterial Spin Labeling) method capable of providing images of perfusion (blood flows in tissue) or blood vessels.

Especially, in the present invention, the present inventor made an invention on the ASL method, which should be refereed to as an ASTAR (modified STAR using Asymmetric Inversion slabs) method based on a STAR (Signal Targeting Alternating Radio frequency) technique known as one ASL method.

Magnetic resonance imaging is a technique for magnetically exciting nuclear spins of a subject placed in a static magnetic field by applying a radio-frequency signal with the Larmor frequency, and obtaining images using FID (free-induction decay) signals or echo signals induced with the excitation.

One category of the magnetic resonance imaging is ASL (Arterial Spin Labeling) imaging. This imaging provides perfusion (tissue blood) images in which blood vessels and microcirculation of a subject are reflected, without injecting contrast medium into the subject, i.e., with non-invasiveness.

This ASL method includes a "continuous ASL (CASL) technique" and a "dynamic ASL (DASL) technique." The CASL technique is a way of applying a largely continuous adiabatic RF wave, while the DASL technique is that of applying a pulsed adiabatic RF wave that can easily be practiced by a clinical MRI system.

The DASL technique includes two main techniques of STAR (Signal Targeting with Alternating Radio frequency) and FAIR (Flow sensitive alternating Inversion Recovery). These two techniques are further deformed into the following various modes.

The STAR technique is a way of imaging one-way flow (normally, an inflow direction of the arteries) with the use of a tagging RF pulse spatially offset from an imaging plane, as proposed by "Nishimura et al., MRM 7:472–484 (1988)" and "Edelman et al., MRM 31:233–238 (1994)." However, in this case, owing to differences in MT (magnetization transfer) effects which will be caused by the tagging RF pulse, there occur signal errors of larger scales than the flow. Particularly, since the tissue blood flow is imaged based on flow signal components provided by differences in minute signals corresponding to orders that are 2% or less of the original signal, differences in the MT effects have a large influence on it.

A way to eliminate the differences in the MT effects is proposed by "Edelman et al., Radiology, 192, 513–520 (1994)," which is an imaging method known as an EPISTAR (echo-planar imaging and signal targeting with alternating radio frequency) technique. In this technique, to try to eliminate differences in the MT effects, RF pulses symmetric in both thickness and offset amount are applied to the upstream and downstream locations of blood flows (artery flows) passing through an imaging plane, respectively. This application enables differences in the MT effects in the imaging plane to be eliminated or lowered, but, like the FAIR technique, resulting in that the blood flows in both the inflow directions into the imaging plane are imaged as well. Thus the effect of prohibiting the veins from being imaged, which is known as vein suppression, will be lost.

Meanwhile, compared to the STAR technique, the FAIR (flow-sensitive alternation inversion recovery) technique proposed by "Kwong et al., MRM 34, 878–887 (1995)," for instance, hardly occur differences in the MT effects, thus lessening a transit delay time, because on-resonance IR pulses are employed as controlling/tagging RF pulses. However, because it is not impossible to separate blood inflow directions into an imaging slice, there arises a problem that using this technique alone cannot accomplish the vein suppression. In addition, when an inflow direction of a dominant blood vessel into a region of interest is desired to be determined, this is also impossible.

In the ASL technique, it is therefore important that the conflicting problems of canceling the MT effects and imaging only one-way flow are solved. A manner of solving or improving these two problems is proposed as, for example, techniques of "New EPI-STAR" and "ASI-STAR." Of these, the New EPI-STAR technique is described by Mai et al., ISMRM 1998, p1205," for example. In this technique, the nature of an adiabatic pulse is utilized to apply an IR pulse of 360 degrees to a tagging side and to apply two IR pulses of 180 degrees to the identical location in the controlling side to that in the tagging side, so that the MT effects are cancelled. This way corresponds to an improved EPISTAR technique, which allows flows from the tagging side to be imaged and enables multislice imaging.

Moreover, the ASI-STAR technique is considered an improved FAIR technique. This technique is performed such that a non-selective IR pulse is applied to a thickened region and a tagging pulse causes a larger offset in an inflow side. This allows the vein inflow side to be located approximately by a selective IR pulse.

However, the foregoing New EPI-STAR technique and ASI-STAR technique have drawbacks that will be described below. Where the New EPI-STAR technique is used to conduct single-slice imaging, two 180-degree pulses consecutively applied cannot provide a completely restored longitudinal magnetization Mz in the controlling-side region. Compared to a condition under which no pulse is applied, influence of an incomplete cancellation of MT effects appears as an amount that cannot be ignored and the RF power increases, leading to a larger SAR. In cases where multislice imaging is conducted, it basically increases a transit delay time, which is unfavorable to quantification.

On one hand, in imaging with the ASI-STAR technique, a frequency offset is given for only one side region. Hence, even if an amount of the offset is small, a difference in the MT effects between the controlling and tagging applications is left as an amount that is small, but cannot be canceled well, which cannot therefore be ignored completely. This amount becomes a major error factor in detecting blood that flows slowly. Moreover, as to the profiles of both vein-side tagging and controlling slabs, their slopes do not coincide with each other completely or approximately completely. As a result, veins that flow at slower speeds are excited, making it impossible to completely cancel the differences between the tagging and controlling applications.

SUMMARY OF THE INVENTION

The present invention is made to consider the foregoing problems caused by the prior art techniques. An object of the present invention is to provide highly quantified perfusion images or blood flow images (MRA) in which not only MT effects in an imaging region are mutually canceled steadily so as to lower difference errors due to signals from stationary tissue but also sensitivity is given to only one-way blood flows so as to extremely reduce the influence of veins, for example, a flow component composed of almost arteries being produced, without largely raising the power of RF waves and/or increasing SAR (RF exposure) excessively.

The present invention is to provide a technique for obtaining perfusion (tissue blood flows) or blood flow images (MRA) on the basis of the ASL technique; those images are non-invasively provided with no contrast medium injected.

In order to accomplish the foregoing objects, the present invention adopts two types of imaging techniques both belonging to the ASL method. One is an approach on a novel ASL method, which is referred to as an ASTAR (Signal Targeting with Alternated Radio frequency using Asymmetric Inversion Slab) technique by the present inventor, while the other one is an approach on novel signal processing conducted with the foregoing EPISTAR method.

1. Approach on ASTAR Technique

First, the ASTAR technique will be now be described.

The ASTAR technique according to the present invention can be applied to either the PASL technique using pulsed adiabatic RF waves or the CASL technique using large continuous adiabatic RF waves. The ASTAR on the PASL technique will be first described, then that on the CASL technique will follow.

1.1. ASTAR on PASL Technique (Outline of ASTAR Technique)

FIG. 1 shows a positional relationship of slabs (or slices set spatially on the ASTAR technique on the basis of the PASL technique. In the figure, the lateral axis is assigned to the body axis direction z of a subject to be imaged, whilst the longitudinal axis at the center of an imaging slab in the z-axis direction is assigned to offset amounts of a modulation frequency. Two oblique dashed lines represent intensities of IR (inversion recovery) gradients.

According to this ASTAR (on PASL) technique, as shown in FIG. 1, an imaging slab is selectively set as an imaging region, and both a tagging slab (or Tag-IR slab) produced by an applied tagging IR pulse (for inversion) and a controlling slab (or Control-IR slab) produced by an applied controlling IR pulse is selectively set to the imaging slab.

Then, a first scan using a first pulse sequence composed of a train of pulses including a tagging IR pulse to be applied slice-selectively to the tagging slab and an imaging pulse train to be applied slice-selectively to the imaging slab (hereinafter, this scanning is referred to as a tagging (labeling) scan) and a second scan using a second pulse sequence composed of a train of pulses including a controlling IR pulse to be applied slice-selectively to the controlling slab and an imaging pulse train to be applied slice-selectively to the imaging slice (hereinafter, this scanning is referred to as a controlling scan) are performed sequentially in time in an appropriate order. An imaging mode for the tagging scan is called tagging mode, while that for the controlling scan is called controlling mode.

In performing the tagging and controlling scans, one characteristic is that, with offset frequencies of both the tagging and controlling IR pulses measured from the center of the imaging slab made to agree to each other, the slab thickness and positional offset of each imaging pulse are changed by the same scale factor. This allows the distances between the tagging-imaging slabs and the controlling-imaging slabs to be adjusted, thus making it equal or approximately equal to each other MT effects caused in the imaging slab by the application of both the IR pulses and making it possible that only one-way blood flows are imaged.

In cases where, for instance, the head of a subject is imaged with this ASTAR technique, the tagging IR slab is located at an inferior limb side (body's lower side) position to an imaging slab, while the controlling IR slab is located at a parietal region side (body's upper side) position. In the present invention, locating the controlling IR slab so that it does not cover the parietal region containing veins is one characteristic that should be maintained. In other words, the controlling IR slab is placed at positions out of the parietal region.

In the ASL method, what should be excluded is normally a signal detected from veins. This "exclusion" is, however, in the end, realized if a signal from the veins does not come into an imaging slab during an interval of inversion time (TI). In comparison with the arteries, the veins flow at relatively slower speeds, so that it is not always necessary to apply a controlling slab at a position completely apart from the head. Namely, the position can be determined with which an appropriate margin separated from an imaging slab, depending on flow speeds of veins, the distance of a spatial gap, inversion time, and others.

Incidentally, in the following description, if required, a subject's region or spatial region at which the controlling slab is located to the imaging slab is simply called "controlling side," while a subject's region or spatial region at which the tagging slab is located to the imaging slab is simply called "tagging side." Further, according to the necessities, images based on echo data acquired by the controlling scan and tagging scan are called "controlling image" and "tagging image," respectively.

(Necessary and Sufficient Condition Satisfying ASTAR Technique)

For each of the controlling and tagging sides, let reference signs in FIG. 1 be:

$BW_{cont}, BW_{tag}$: band widths [Hz] of controlling and tagging IR pulses;

$G_{cont}, G_{tag}$: gradient intensities [Hz/cm] for slab selection at application of IR pulses;

$deltaF_{cont}, deltaF_{tag}$: offset amounts [Hz] of modulation frequency measured from center of imaging slab;

$Offset_{cont}, Offset_{tag}$: distance [cm] between centers of imaging and controlling slabs and distance [cm] between centers of imaging and tagging slabs;

$Thick_{cont}, Thick_{tag}$: thicknesses [cm] of control and tagging slabs; and $Gap_{cont}, Gap_{tag}$: distances [cm] of gaps from imaging slab to each controlling slab of tagging slab, then the relationships of:

$$Offset_{cont} \cdot G_{cont} = deltaF_{cont} \quad (a)$$

$$Thick_{cont} \cdot G_{cont} = BW_{cont} \quad (b)$$

$$Offset_{tag} \cdot G_{tag} = deltaF_{tag} \quad (c)$$

$$Thick_{tag} \cdot G_{tag} = BW_{tag} \quad (d)$$

$$Gap_{cont} = Offset_{cont} - (Thick_{image} + Thick_{cont})/2 \quad (e)$$

$$Gap_{tag} = Offset_{tag} - (Thick_{tag} + Thick_{tag})/2 \quad (f)$$

are realized.

In order to make MT effects caused by the controlling and tagging scans equal in amount to each other, it is necessary and sufficient that the band widths BW and offset frequencies of IR pulses for locating the controlling and tagging IR slabs are equal to each other, respectively, that is, $$BW_{cont} = BW_{tag} \quad (g)$$

$$deltaF_{cont} = deltaF_{tag} \quad (h)$$

are realized.

Thus, from the foregoing expressions (a) to (f), $$Offset_{cont} \cdot G_{cont} = Offset_{tag} \cdot G_{tag} \quad (i)$$

$$Thick_{cont} \cdot G_{cont} = Thick_{tag} \cdot G_{tag} \quad (j)$$

are obtained.

Incidentally, it is required for the ASTAR technique that the IR pulses used for the controlling and tagging scans (controlling and tagging IR pulses) be applied with their application polarities opposite to each other in relation to an imaging slab. For example, if the body axis direction is assigned to the z-axis direction, the center of an imaging slab is determined as the origin, and the upstream and downstream directions of blood flows to be suppressed (for instance, veins) are assigned to the positive and negative, respectively, the expressions of $$Offset_{cont} > 0,\ Offset_{tag} < 0 \quad (k)$$

should be realized. As long as MT effects keep symmetrical with respect to the positive and negative offset excitation frequencies (deltaF) of the IR pulses, both equal absolute values and opposite sings enable those expressions to be realized. But if asymmetrical, the offset excitation frequencies (deltaF), even their signs, should be equal to each other.

Additionally, as stated before, the ASTAR technique requires one more condition that the controlling slab be not located at a parenchyma region containing the veins in the controlling side. Hence, when a limited distance from the z-axis center of an imaging slab to the controlling slab is expressed by $D_{limit}$, the above condition can be met if an expression of:

$$Offset_{cont} > D_{limit} + Thick_{cont}/2 \quad (l)$$

is fulfilled.

Therefore, when summarizing the foregoing various conditions in the forms in which the relationships among gradients G, thicknesses Thick, and offsets Offset are included, a necessary and sufficient condition for not only making the amounts of MT effects, caused in an imaging slab when the controlling and tagging scans are performed, equal to each other but also detecting only a signal component from blood flow inflowing from the tagging side can be expressed as follows:

$$Offset_{cont} / Offset_{tag} = Thick_{cont} / Think_{tag}$$
$$= Gap_{cont} / Gap_{tag}$$
$$= G_{tag} / G_{cont}$$
$$= N\ (N:\ negative\ real\ number) \ldots \quad (m)$$

and $$Offset_{cont} > D_{limit} + Thick_{cont}/2$$

$$Offset_{tag} < 0 \quad (n),$$

in which the controlling side is designated as being positive.

As to the above expression (1), it is an ideal state in which the controlling slab is not completely overlapped on the vein that is not an objective for imaging. On the contrary, this condition is flexible to some extent. If blood to be suppressed flows at a slower speed, it is still enough that the condition is not so strictly established. It is enough only if the blood tagged by the controlling IR pulse does not reach an imaging slab during an inversion time (TI) thereof Thus, it is sufficient to determine the limited distance $D_{limit}$ by considering both an organ to be objective and an inversion time thereof. When taking a maximum velocity of blood flow to be suppressed as being v, a practical limited distance $D_{limit}$ is expressed by $$D_{limit} = v \cdot TI \quad (o).$$

In general, because the flow speed of the vein is lower, it is not required to offset the control slab beyond a necessary value.

(Date Acquisition and Processing Employed by ASTAR Technique)

This ASTAR technique employs, (i) to lessen misregistration, a way of, called interleaved manner, acquiring data of controlling and tagging images by alternating sequentially in time, shot by shot, the controlling and tagging scans.

Moreover, (ii) in order to obtain images of an imaging slab, difference calculation is performed between controlling and tagging image data. In the present invention, complex-number difference calculation (individual differences for real numbers and imaginary numbers) is executed at the stage of raw data, which is realized by an additional function for processing echo data (i.e., raw data before reconstruction), which is standard-provided in ordinary MRI systems. In other words, when $S_{cont}$ and $S_{tag}$ represent raw data of controlling and tagging images, differences deltaS produced by the complex-number difference calculation is expressed by:

$$deltaS = |S_{cont} - S_{tag}| \quad (p).$$

Alternatively, such difference calculation may be performed after computation of absolute values, that is, $$deltaS = |S_{cont}| - |S_{tag}| \quad (q).$$

In the expressions (p) and (q), it is meant that the processing of absolute values is practically performed after the reconstruction of raw data.

Alternatively, the foregoing difference calculation may be carried out at the stage of image data reconstructed from the raw data.

Furthermore, particularly, (iii) to improve the SNR of a perfusion image, an averaging method is employed, in which each of the controlling and tagging scans is performed a plurality of times to undergo averaging processing.

Where the averaging method is employed and the difference calculation is performed on the above expression (p) (the absolute values are calculated after the difference calculation), differences between the raw data are calculated (complex-number difference calculation), and then added (averaging). This enables continuous data acquisition for each one averaging, shortening the entire time necessary from scanning to data processing. In contrast, in the case of calculating differences based on the above expression (q), such a function of addition cannot be used. In this case, after averaging each of controlling and tagging images, absolute values should be calculated, and then subject to difference calculation.

(Suppression of Signals from Large Blood Vessel in Perfusion Imaging) Needless to say, signals detected from large blood vessels, such as arteries or veins, are indispensable for MRA imaging to observe the blood vessels. However, for perfusion imaging to allow blood capillaries and/or tissue blood to be observed, the signals from those large blood vessels are normally regarded as obstructive signals in the field of clinics.

In the ASTAR technique according to the present invention, the perfusion imaging adopts a way of suppressing signals from the large blood vessels. Specifically, the reconstructed image data deltaV of raw data obtained by the expressions (p) and (q) include signals detected from a large blood vessel (for example, artery) inflowing from the tagging side to an imaging slab. This signals are supposed to be suppressed. When taking an upper limit of a signal from a large blood vessel to be suppressed as $deltaV_{high}$, only a signal component satisfying $$deltaV=(deltaV<deltaV_{high}) \qquad (r)$$

is extracted. This processing provides perfusion images of which influence of the signal from such a large blood vessel is reduced.

1.2. ASTAR on CASL Technique

On one hand, the ASL imaging according to the present invention can be practiced with the ASTAR based on the CASL (continuous ASL) technique.

In the case of the CASL technique, a continuous wave (CW) having a single frequency that satisfies a given adiabatic condition is continuously applied to the inflow-side portion of an artery for more than a certain period. This application causes spins in the blood flow to be inverted, which then inflow into a downstream imaging slab.

Imaging on this CASL technique is provided with two ways: (1) one way is to use a small transmitting RF coil having no sensitivity on an imaging slab, where, without applying a gradient, the RF coil is such excited that the sensitivity region thereof includes inflowing arteries such as carotid arteries (for instance, refer to "MRM 33, 209–214 (1995)"); and (2) the other way is to use an ordinary head-dedicated RF coil to apply a continuos wave together with a gradient (for instance, refer to "Radiology 1998; 208: 410–416"). In the latter, if the continues wave is applied concurrently with a gradient in the cephalocaudal direction (Z-axis direction), spins residing in a thin tagging slice (theoretically, a plate, but refereed to as a slab, for the sake of convenience) nearly perpendicular to blood flows such as arteries are excited, as shown in FIG. 18, and then the blood flows of which spins are inverted through the slice flow into an imaging slab.

Although the PASL technique requires that spins existing in a slab of a certain thickness be inverted, actual slabs (tagging and controlling slabs) in which spin inversion occurs become extremely thin, as shown in FIG. 18. Hence, under the PASL technique, blood present at an inflowing side in the tagging slab, which is far from the imaging slab, takes more time to reach the imaging slab, during which time the T1 relaxation of the spins proceeds to a greater extent, resulting in that the SNR of blood flow images is lowered. However, the CASL technique is able to lessen the influence of this problem caused by the inflowing delay.

In the case of the CASL technique, like the PASL technique, imaging of only blood flows with the use of the RF coil above-described in either way (1) or (2) involves difference calculation between two images of which objective blood flows are not tagged (not inverted) (controlling mode) and tagged (tagging mode). This permits signals from stationary tissue to be cancelled. If using the small RF coil described in the above way (1), differences in signal caused by MT effects can be almost ignored, as long as the sensitivity region of the coil is shifted from the imaging slab. On the contrary, when the head-dedicated RF coil described in the above way (2) is used and moreover, a transmitting sensitivity in RF application to the tagging slab covers a region including an imaging slab, it is needed that MT effects influencing the imaging slab be canceled. Namely, the MT effects in the controlling mode should be controlled to the same amount as that in the tagging mode. Even in this case, like the PASL technique, it is essential that one of arteries or veins, for example, veins, be suppressed,so that they are not depicted.

Where the ASTAR technique is performed on the CASL technique involving the use of the head-dedicated RF coil described in the above way (2), it is considered that the excited slabs (tagging and controlling slabs) by the PASL technique are equivalently changed into thin plates (refer to FIGS. 1 and 18).

In applying the CASL technique to the EPISTAR later described, because setting of $Offset_{tag}=Offset_{cont}$ is indispensable, it is impossible to suppress the depiction of veins inflowing from the controlling side. Hence practicing the ASTAR on the CASL technique, by which a state of $Offset_{tag}<Offset_{cont}$ can be established, is effective, because the advantages of both of them can be obtained.

2. Approach on EPISTAR Technique

An approach on the EPISTAR technique will now be described. This approach is based on post-processing of signals acquired by scanning on the EPISTAR technique, which accomplishes the object of the present invention.

2.1. Depiction of Blood Flow in One Direction on Signal Processing

FIG. 2 pictorially shows slabs spatially located on basis of the EPISTAR technique under the similar dimensions to those in FIG. 1

Based on the EPISTAR technique, as described before, canceling differences in MT effects needs both controlling and tagging slabs symmetrically located with respect to an imaging slab, the controlling slab having an identical (symmetrical) slab thickness and a distant offset amount with those of the tagging slab. When calculating differences between as-acquired controlling and tagging images with an ordinary ASL technique, blood flows inflowing into the imaging slab in the two inflow directions are both imaged.

Therefore, in the present invention, with which the symmetry of the slab thicknesses and distance offset amounts is still mainlined, which are characteristic of the EPISTAR technique, scanning is performed to acquire data of controlling and tagging images, and a characteristic processing is such performed that only a signal component corresponding to a desired blood flow is extracted in the stage of processing the data for visualization.

Let assume that raw data (complex data) acquired by tagging and controlling scans are $S_{cont}$ and $S_{tag}$, respectively, and their reconstructed image data are $V_{cont}$ and $V_{tag}$, respectively. If the signal processing for these image data includes calculating differences, before calculating absolute values, that is, $$deltaV=|V_{cont}-V_{tag}| \qquad (s)$$

is calculated, the signals of blood flows inflowing into an image slab in both of the directions are mixed with an image thereof. Instead of this, calculating the absolute values of the reconstructed image data $V_{cont}$ and $V_{tag}$ before the difference calculation, that is, $$\text{delta}V=|V_{tag}|-|V_{cont}| \tag{t}$$

may be performed. Thus, with respect to a signal component of blood inflowing from the controlling side, it is true that $$\text{delta}V<0 \tag{u},$$

while, concerning a signal component of blood inflowing from the tagging side, $$\text{delta}V>0 \tag{v}$$

is established. Thus, obtaining data components deltaV fulfilling this expression (v) enables blood inflowing from the tagging side (normally, assigned to arteries) to be extracted separately.

(Perfusion Image)

As described before, compared to large blood vessels, such as arteries and veins, signals acquired from flows of thin blood vessels, such as blood capillaries and blood flows in tissue, are considerably lower in intensity. In addition, their flowing directions are not restricted to one, and those types of blood are supposed to flow into each voxel composing an imaging slab from every direction. Hence simply extracting signal components satisfying deltaV>0 from the data deltaV calculated with the expression (t) results in that perfusion components on blood inflowing from the controlling side are suppressed, and are difficult to reflect on an perfusion image.

In perfusion imaging, what should be suppressed from a clinical point of view are signals detected from large blood vessels (arteries and veins). Thus, signal processing is performed such that perfusion components on blood inflowing into an imaging slab from both of the directions remain on a perfusion image and only signals from large blood vessels are suppressed thereon. In the present invention, this processing is done with thresholds. Practically, for the above expression (t) of:

$$\text{delta}V=|V_{tag}|-|V_{cont}|,$$

only signal components meeting an expression of:

$$\text{delta}V=(-\text{delta}V_{low}<\text{delta}V<\text{delta}V_{high}) \tag{w},$$

where $\text{delta}V_{low}$:upper limit of perfusion signals
$\text{delta}V_{high}$:lower limit of large blood signals
are extracted.

In order to accomplish the foregoing object, the present invention adopts the following configurations based on the foregoing principles.

First, according to an approach on the ASTAR technique, there is provided an MRI system for obtaining an ASL (Arterial Spin Labeling) image of an imaging slab of an subject placed in a static magnetic field by locating a tagging slab and a controlling slab at one side and the other side of the imaging slab, the system comprising: setting means for setting a first RF wave and a first magnetic gradient both for selective-exciting the tagging slab and a second RF wave and a second magnetic gradient both for selective-exciting the controlling slab, in which offset amounts of exciting central frequencies of both the first and second RF waves to a central position of the imaging slab are equal to each other and offset positions of the tagging slab and the controlling slab to the imaging slab are different from each other; a first scanning means for performing a pulse sequence including he first RF wave and the first magnetic gradient so as to acquire a first MR signal from the imaging slab; a second scanning means for performing a pulse sequence including the second RF wave and the second magnetic gradient so as to acquire a second MR signal from the imaging slab; image data producing means for producing image data based on mutual difference between the first and second MR signals; and visualizing means for visualizing the image data as an ASL image.

A preferred one example is that each of the first and second RF waves consists of a single-frequency continuous RF wave determined correspondingly to each of the first and second magnetic gradients so as to excite a desired slab position.

Another preferred example is that the setting means set conditions concerning the first and second RF waves and the first and second magnetic gradients such that a ratio between slab thicknesses of the tagging and controlling slabs and a further ratio between the positional offsets of the tagging and controlling slabs to the imaging slab are equal to each other. In this case, for example, each of the first and second RF waves consist of a pulsed wave having a certain frequency band.

In the above configurations, each of the first and second RF waves may be an IR wave inverting spins, and the first and second scanning means may be configured to apply the IR pulse in mutually opposite polarities to the imaging slab. In this case, preferably, the imaging slab is located at a head portion of the subject, and the setting means have means for setting the controlling slab separately from the head portion.

Moreover, in each configuration stated above, the image data producing means may comprise means for extracting from a difference of the MR signal a signal component of not more than a threshold determined as a minimum signal intensity for a blood vessel to be suppressed of the subject. This provides a perfusion image.

Further, in each configuration stated above, it is preferred that each of the first and second scanning means include means for performing the same type of pulse sequence enhancing a longitudinal magnetization of the spins of the subject as well as including each of the first and second RF waves. For example, each of the first and second RF waves is an IR wave for inverting spins, the IR wave being applied slice-selectively. A preferred example is that each of the pulse sequences includes a pre-saturation pulse for previously saturating spins of the subject.

Further, in each configuration stated above, the first and second scanning means may comprise means for performing the pulse sequences every application of the RF waves in an interleave system.

Still further, in each configuration stated above, each of the first and second scanning means may be configured to perform a plurality of times the acquisition of the MR signal from the imaging slab, and the image data producing means may include means for averaging the MR signal acquired the plurality of times. This is able to improve an SNR.

In the foregoing configurations according to the PASL technique, the setting means is able to comprises means for providing as known amounts a slab thickness of the imaging slab, a slab thickness of the tagging slab, a distance between the imaging and tagging slabs, and a distance between the imaging and controlling slabs; and calculating means for calculating a slab thickness and a positional offset amount of the controlling slab on the basis of the known amounts.

Still, according to a preferred example, there is provided a pulse sequence in which, between application of each of the first and second RF waves and application of an imaging pulse train, a non-slice selective IR wave to be applied to a region of the subject including the imaging slab, tagging slab, and controlling slab is placed. In this configuration, preferably, an interval from application of the non-slice selective IR pulse to application of the imaging pulse train in the pulse sequence can be determined so that a spin-lattice relaxation time of stationary tissue contained in the imaging slab becomes an amount regarded as being approximately zero on average at a time of applying the imaging pulse train. This is able to steadily reduce difference errors specific to the stationary tissue, and provide an ASL image in which blood flow is mainly depicted. For example, the non-slice selective IR wave consists of a plurality of non-slice selective IR waves. Of course, one non-slice selective IR wave may be applied.

On one hand, according to an approach on the EPISTAR technique, provided is an MRI system comprising: a first scanning means for applying a first RF wave to a tagging slab to be located in one side of an imaging slab of a subject so as to acquire a first MR signal from the imaging slab; a second scanning means for applying a second RF wave to a controlling slab to be located, symmetrically to the tagging slab, in the other side of the imaging slab so as to acquire a second MR signal from the imaging slab; and image data producing means for producing image data on the basis of the first and second MR signals, wherein the image data producing means comprise a first and second absolute-value calculating means for calculating absolute values of the first and second MR signals after reconstruction thereof, respectively; difference means for performing mutual differences between the absolute values of the first and second MR signals; and extracting means for extracting image data of a desired signal component from differences obtained by the difference means.

In this configuration, for example, the extracting means are configured to make the differences obtained by the difference means have threshold processing with a threshold determined to suppress a signal of a large blood vessel inflowing from a controlling slab side into the imaging slab, so that a signal component of a blood flow inflowing from a tagging slab side into the imaging slab is extracted. Further, the extracting means may be configured to make the differences obtained by the difference means have threshold processing with a threshold determined to suppress a signal of a large blood vessel inflowing into the imaging slab, so that a signal component of perfusion inflowing into the imaging slab is extracted.

Furthermore, according to the ASTAR technique of the present invention, provided is a n MR imaging method of obtaining an ASL (Arterial Spin Labeling) image of an imaging slab of an subject placed in a static magnetic field by locating a tagging slab and a controlling slab at one side and the other side of the imaging slab, comprising the steps of: setting a first RF wave and a first magnetic gradient both for selective-exciting the tagging slab and a second RF wave and a second magnetic gradient both for selective-exciting the controlling slab, in which offset amounts of exciting central frequencies of both the first and second RF waves to a central position of the imaging slab are equal to each other and offset positions of the tagging slab and the controlling slab to the imaging slab are different from each other; performing both a pulse sequence including the first RF wave and the first magnetic gradient so as to acquire a first MR signal from the imaging slab a pulse sequence including the second RF wave and the second magnetic gradient so as to acquire a second MR signal from the imaging slab; producing image data based on mutual difference between the first and second MR signals; and visualizing the image data as an ASL image.

DETAILED DESCRIPTION OF THE PREFERRED EMBODIMENTS

Hereinafter, embodiments of the present invention will now be described with reference to the accompanying drawings.

(First Embodiment)

In reference to FIGS. 3–8, a first embodiment will now be described. An MRI (magnetic resonance imaging) system of the present embodiment is characteristic of providing blood vessel images (MRA images) or perfusion images (images of blood in tissue) on the basis of the foregoing first approach of the present invention, i.e., the ASTAR technique.

Figure 3:
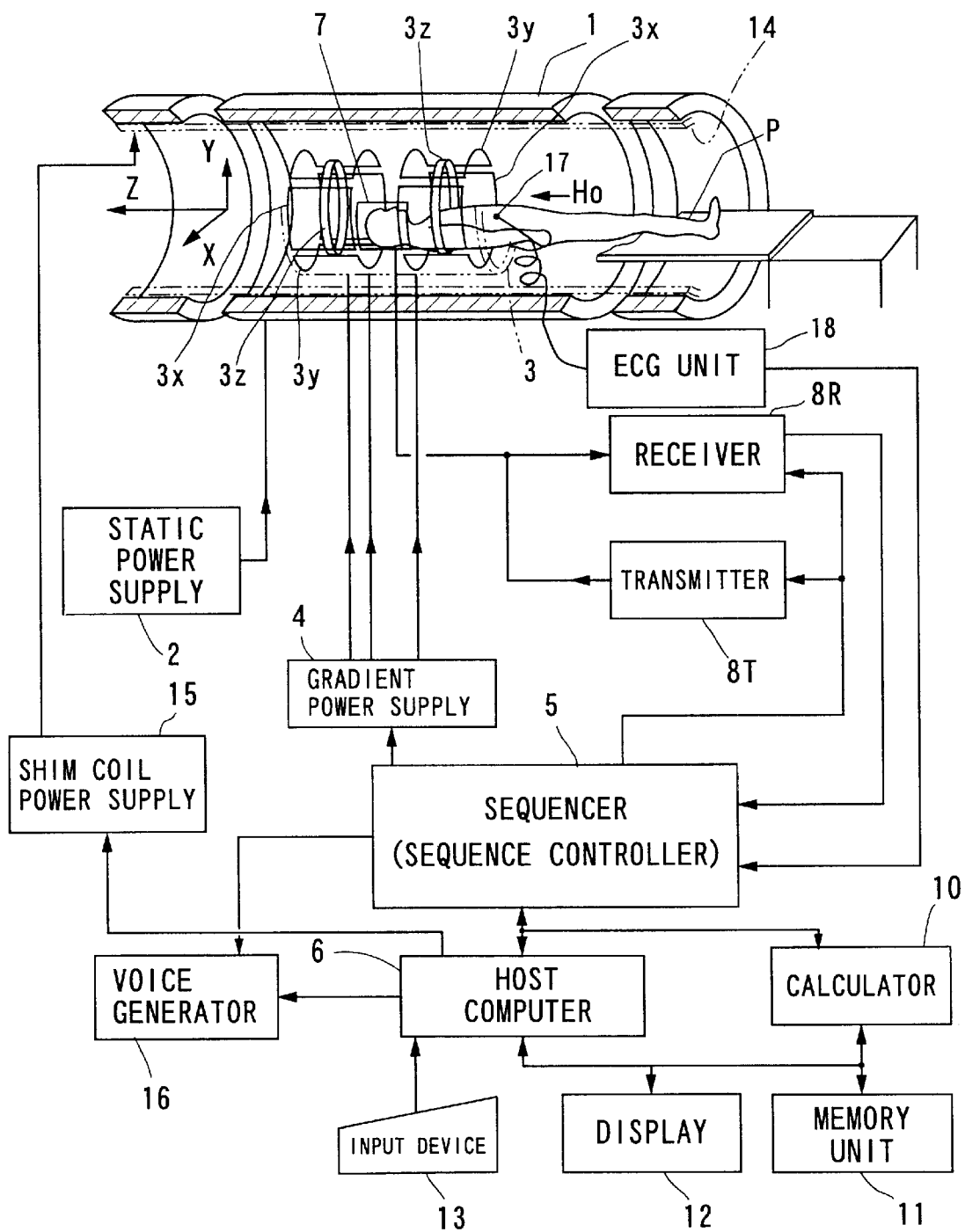
FIG. 3 is a block diagram illustrating one example of an MRI system according to embodiments of the present invention.

The outlined configuration of the MRI system is shown in FIG. 3. The MRI system comprises a patient couch on which a patient P lies down, static magnetic field generating components for generating a static magnetic field, magnetic field gradient generating components for appending positional information to the static magnetic field, transmitting/receiving components for transmitting and receiving radio-frequency signals, and control and operation components responsible for control of the whole system and for image reconstruction.

The static magnetic field generating components includes a magnet 1 that is of, for example, a superconducting type, and a static power supply 2 for supplying a current to the magnet 1, and generates a static magnetic field $H_0$ in an axial direction (Z-axis direction) in a cylindrical bore (diagnostic space) into which the patient P is inserted. The magnet unit includes shim coils 14. A current used to homogenize a static magnetic field is supplied from a shim coil power supply 15 to the shim coils 14 under the control of a controller to be described later. The couch top of the patient couch on which the patient P lies down can be inserted into the bore of the magnet 1 so that the couch top can be withdrawn.

The magnetic field gradient generating components includes a gradient coil unit 3 incorporated in the magnet 1. The gradient coil unit 3 includes three pairs (kinds) of x-, y-, and z-coils 3x to 3z used to generate magnetic field gradients changing in strength in X-axis, Y-axis, and Z-axis directions that are mutually orthogonal. The magnetic field gradient generating components further include a gradient power supply 4 for supplying current to the x-, y-, and z-coils 3x to 3z. The gradient power supply 4 supplies pulsed currents to the x-, y-, and z-coils 3x to 3z under the control of a sequencer 5 that will be described later.

The pulsed currents supplied from the gradient power supply 4 to the x-, y-, and z-coils 3x to 3z are controlled, whereby magnetic field gradients changing in the three axial directions, that is, the X-, Y-, and Z- physical directions are generated. Thus, logic directions in which a slice magnetic gradient Gs, a phase-encoding magnetic gradient Ge, and a read-out (frequency-encoding) magnetic gradient Gr are applied can be specified and changed arbitrarily. The magnetic gradients to be applied in the slice, phase-encoding, and read-out directions are superposed on the static magnetic field $H_0$.

The transmitting/receiving components includes an RF coil 7 located in the vicinity of a patient P in the scanning space inside the magnet 1, and a transmitter 8T and a receiver 8R both connected to the coil 7. Under the control of a sequencer 5 described later, the transmitter 8T and receiver 8R operate such that the transmitter 8T supplies to the RF coil 7 pulsed RF currents with a Larmor frequency, which are used to excite spins to cause nuclear magnetic resonance (NMR), while the receiver 8R accepts radio-frequency MR signals that the RF coil 7 has received, carries out various kinds of signal processing to produce corresponding digital data to the MR signals.

Furthermore, the control and operation components includes a sequencer 5 (also referred to as a sequence controller), a host computer 6, a controller 10, a memory unit 11, a display 12, and an input unit 13. Among them, the host computer 6 has the function of accepting information given by an operator, providing the sequencer 5 scan sequence information on the accepted information, and managing the operations of the entire system including the calculator 10, memory unit 11, and display 12 as well as the sequencer 5, according to previously installed software procedures.

The sequencer 5, which has a CPU and memories, stores pulse sequence information sent from the host computer 6, and controls a series of operations performed by the gradient power supply 4, transmitter 8T, and receiver 8R according to the stored information. Additionally, the sequencer 5 temporarily receives digital data corresponding to MR signals outputted from the receiver 8R, before transferring them to the calculator 10 that performs reconstruction.

The pulse sequence information includes all information required to operate the gradient power supply 4, transmitter 8T, and receiver 8R according to a series of pulses consisting of a pulse sequence. Such information includes information on the strength, duration, and application timing of pulsed currents applied to the x-, y-, and z-coil 3x to 3z.

Any type of fast-imaging pulse sequence is available for the pulse sequence employed in this embodiment, as long as the T1 (spin-lattice relaxation) time can be enhanced. For example, a fast FE sequence, fast SE sequence, EPI (Echo Planar Imaging) sequence, FASE (Fast Asymmetric SE) sequence, and hybrid EPI sequence can be used.

The calculator 10 performs, in an appropriate order, reading inputted raw data, mapping the raw data in the image Fourier space (known as the k-space or frequency space), averaging of data, calculation of differences between data obtained in tagging and controlling modes, operation of data with a threshold, calculating absolute values of complex-number data, and reconstruction of raw data into actual space data (for example, two-dimensional and three-dimensional Fourier transform). Examples of the processing performed by the calculator 10 are shown in FIGS. 7 and 10 to 12. Incidentally, for three-dimensional imaging, the calculator 10 is able to perform other types of processing including MIP (maximum intensity projection) processing used when two-dimensional image data are produced from three-dimensional image data.

The memory unit 11 is able to preserve image data that have undergone the above processing, besides the raw data and reconstructed image data. The display 12 displays an image. An operator to provide the host computer 6 with necessary information, such as desired scan conditions, scan sequences, and ways of processing images, uses the input unit 13.

In addition, as part of the control and operation components, there are provided a voice generator 16, ECG sensor 17 and ECG unit 18. The voice generator 16 utters a sound message for the breath hold of a patient (a subject to be imaged) in response to a command from the sequencer 5 or host computer 6. Both of the ECG sensor 17 and the ECG unit 18 detect an ECG signal of a patient and send it to the sequencer 5, so that ECG-gating scans can be performed.

The operation of this embodiment will now be described.

In this embodiment, MR imaging that obtains a blood image of an artery in the head will be performed using the ASTAR technique of the present invention. A pulse sequence that will be used is a fast FE sequence with an IR pulse.

Figure 4:
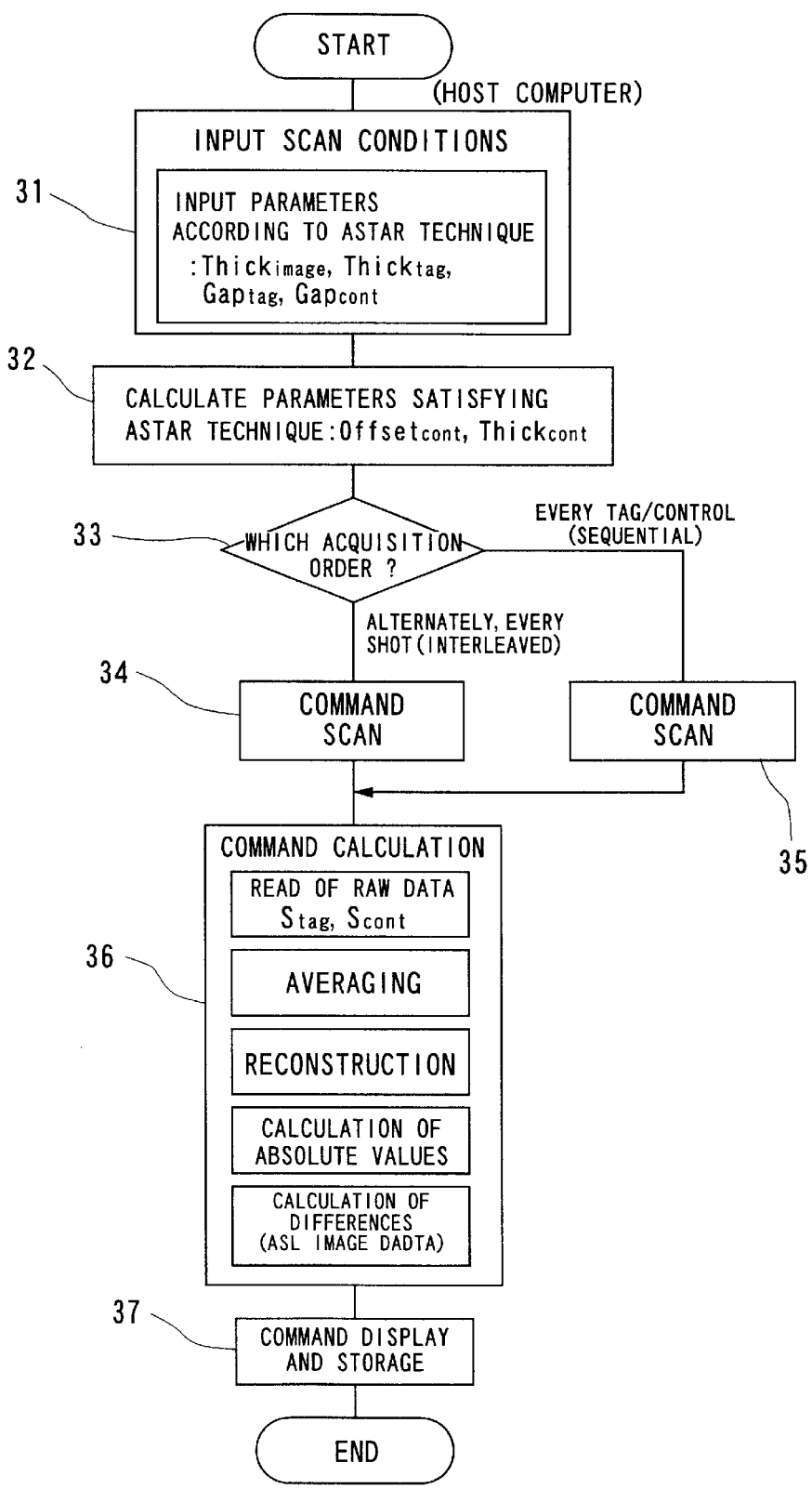
FIG. 4 is a flowchart outlining the processing of a host computer that executes the ASTAR technique (based on the PASL technique) in a first embodiment.
Figure 5:
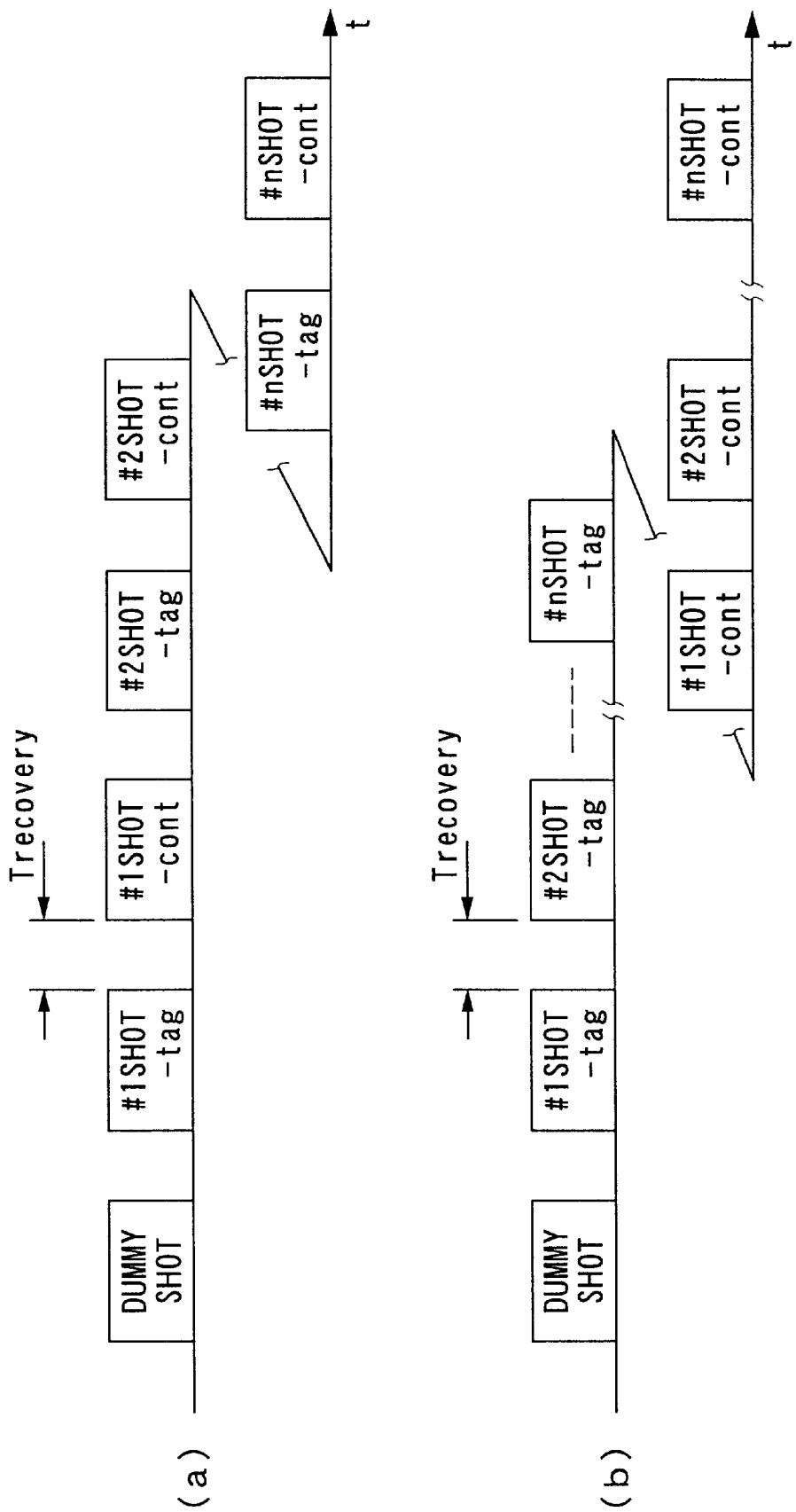
FIG. 5 shows timing charts explaining the scanning order for each shot of tagging and controlling scans.

After the preparation such as a positioning scan, the host computer 6 responds to a command from an operator, and launches image processing shown in FIG. 4.

First, based on operational information given via the input device 13, scan conditions are inputted (step 31). These scan conditions includes, in addition to an imaging position (central position of an imaging slab), the type of pulse sequence, and its parameters (inversion time TI, repetition time TR, echo time TE, recovery time $T_{recovery}$, and flip angle FA(=α) of a flip pulse), and others, the thickness $Thick_{image}$ of an imaging slab, the thickness $Thick_{tag}$ of a tagging slab, the distance $Gap_{tag}$ between the imaging and tagging slabs, and the distance $Gap_{cont}$ between the imaging and controlling slabs, which are specific to the ASTAR technique (refer to FIG. 1).

An operator may set those four parameters through the input device 13 as desired values every time of scanning. Alternatively, when imaging is conducted, those parameters can be set by selection from a memory table formed in the memory unit 11, in which some combinations of desired parameters' values are stored previously.

On completion of those scan conditions, the host computer 6 calculates the rest of the parameters that satisfy the necessary and sufficient conditions of the ASTAR technique (step 32). Namely, the rest are the thickness $Thick_{cont}$ of the controlling slab and the offset distance $Offset_{cont}$ of the controlling slab measured from the central position of the imaging slab (refer to FIG. 1). From the expression (m), $$Thick_{cont} = Offset_{cont}(Thick_{tag}/Offset_{tag}) \quad (a')$$

is obtained. Here, if assuming that $$Offset_{tag} = -\{0.5(Thick_{image} + Thick_{tag})\} \quad (b')$$

$$Offset_{cont} = 0.5(Thick_{image} + Thick_{cont}) + Gap_{cont} \quad (c'),$$

in the case of $Offset_{tag} \neq 0$, two expressions of:

$$Offset_{cont} = (0.5 \cdot Thick_{image} + Gap_{cont})/\{1 - 0.5(Thick_{tag}/Offset_{tag})\} \quad (d')$$

$$Thick_{cont} = (0.5 \cdot Thick_{image} + Gap_{cont})(Thick_{tag}/Offset_{tag})/\{1 - 0.5(Thick_{tag}/Offset_{tag})\} \quad (e')$$

are obtained. In other words, from these expressions (d') and (e'), the thickness $Thick_{cont}$ of the controlling slab and the offset distance $Offset_{cont}$ thereof are calculated.

The host computer 6 then determines an order of data acquisition between the tagging and controlling scans, which is given as one scan condition (step 33). In this embodiment, two types of acquisition order are prepared as shown in FIG. 5(a) and (b), so either type can be selected.

The acquisition order in the FIG. 5(a) adopts an order called "interleaved order," in which, after a dummy shot, the scans in both the tagging and controlling modes are alternately repeated shot by shot at intervals of a certain recovery time $T_{recovery}$. In contrast, the acquisition order in the FIG. (b) adopts an order known as a "sequential order," in which, after a dummy shot, the scans in the tagging mode are executed shot by shot at intervals of a certain recovery time $T_{recovery}$, which is followed by the scans in the controlling mode also executed shot by shot at intervals of a certain recovery time $T_{recovery}$.

When determined at step 33 that the acquisition of "interleaved order" is designated, scanning on the acquisition of the interleaved order shown in FIG. 5(a) is commanded (step 34). Meanwhile, when determined that the acquisition of "sequential order" is specified, scanning on the acquisition of the sequential order shown in FIG. 5(b) is commanded (step 35). This command is done in such a way that the host computer 6 sends to the sequencer 5 information on the pulse sequence in which the parameters of the ASTAR technique that are received and computed, described above, are reflected.

Figure 6:
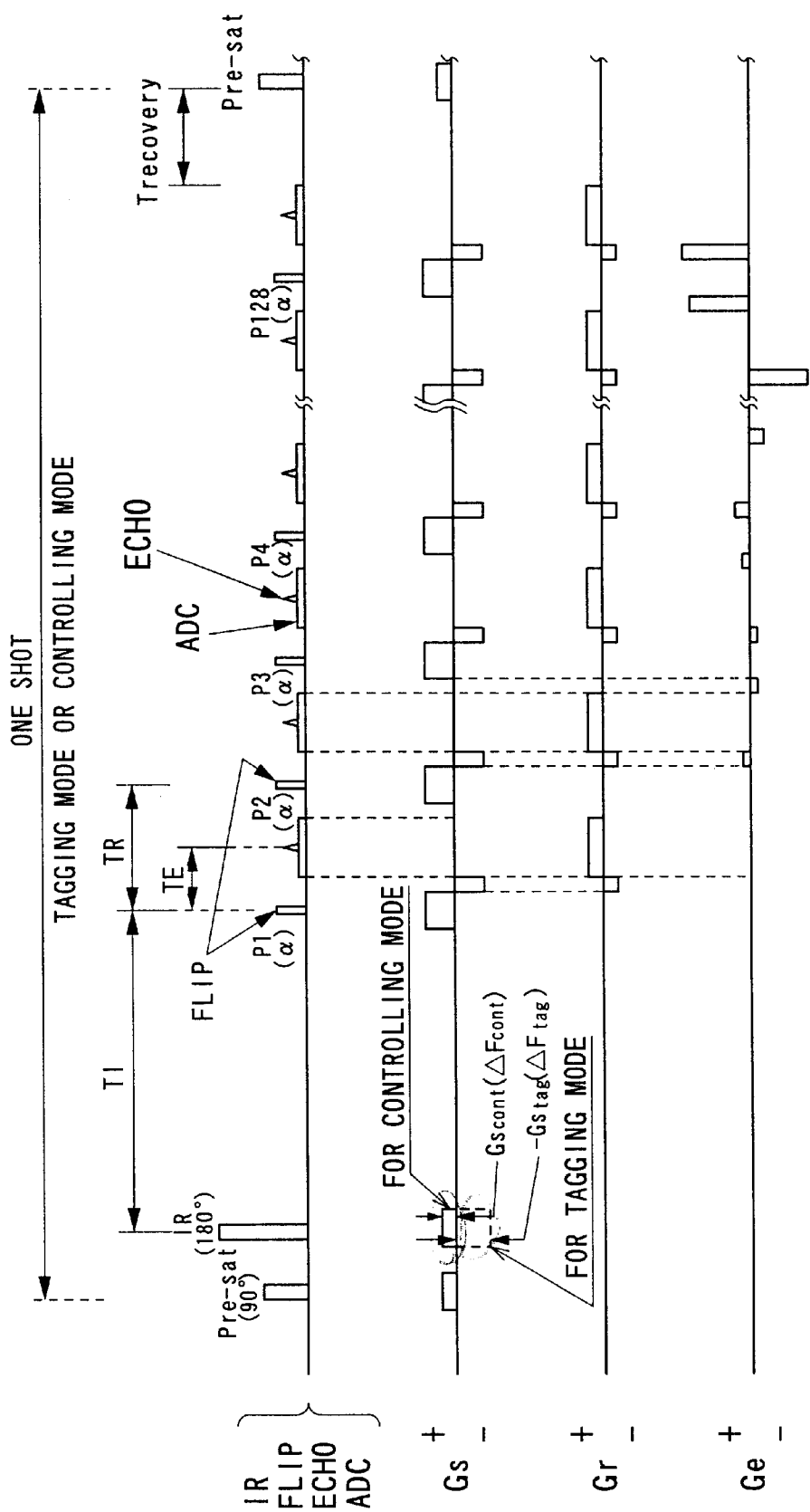
FIG. 6 is a timing chart of a pulse sequence executed at each shot (, which explains both of the tagging and controlling scans)

Responsively to this command, the sequencer 5 starts its driving by which the gradient supplier 4, transmitter 8T, and receiver 8R are each driven on a designated pulse sequence. This enables a two-dimensional scan made up of shots, regardless of the type of acquisition order, on a fast FE pulse sequence using the IR pulse, as shown in FIG. 6, as one example.

The sequence in FIG. 6 will now be described. Let us assume that the acquisition on the interleaved order is commanded. In the first shot in the tagging mode, for example, in response to a command from the sequencer 5, a pre-saturation (previous saturation) pulse Pre-sat is applied together with a slice magnetic gradient Gs lower in magnitude than that Gs to be applied to an imaging slab. By this application, spins residing in a wider region than the imaging slab are previously excited in a slice selective manner.

Figure 1:
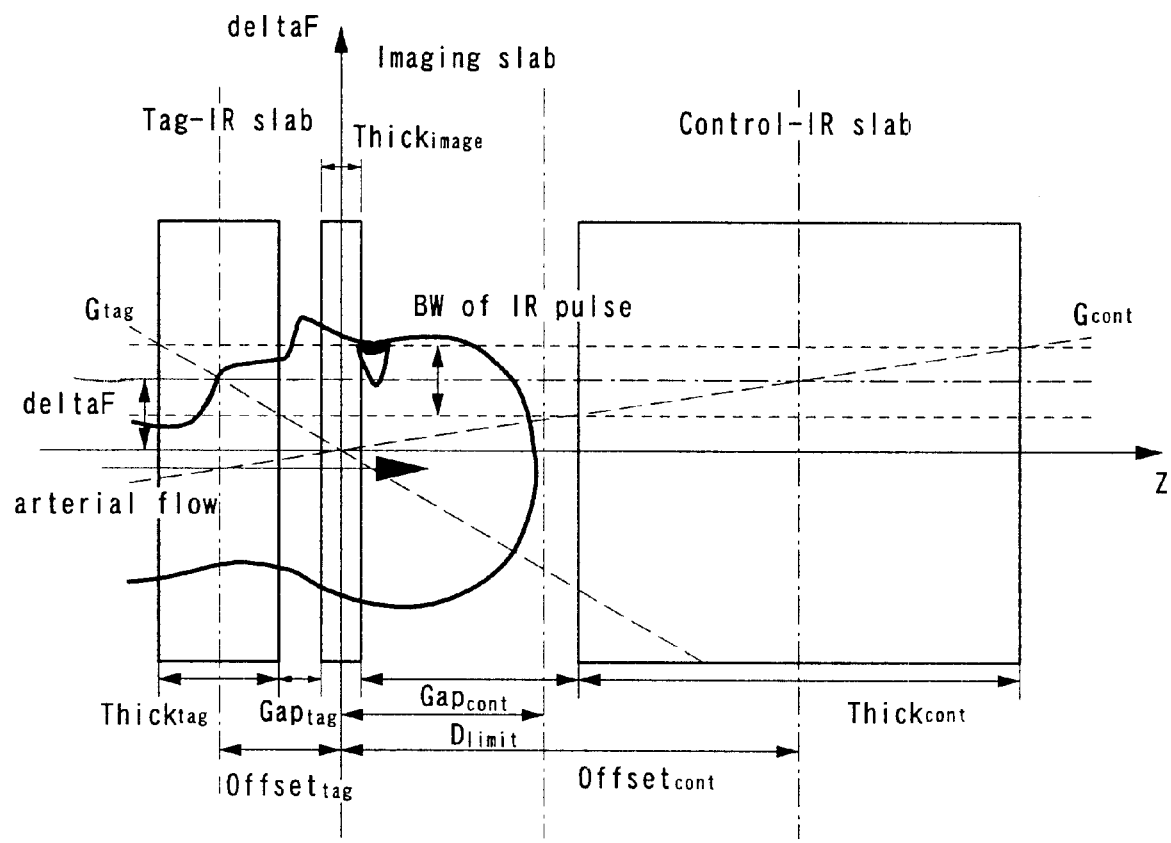
FIG. 1 shows the principle of an ASTAR technique (based on the PASL technique) according to one mode of the present invention.

Then, in response to a command of the sequencer 5, a slice magnetic gradient $Gs = Gs_{tag}$ and a tagging IR pulse (180° RF pulse: an offset value of its modulation frequency=$-deltaF_{tag}$, its bandwidth=$BW_{tag}$) are applied. This enables, as shown in FIG. 1, a tagging slab to be selectively located over a desired thickness in the tagging side to the imaging slab (inferior limb side to the imaging slab; inflowing side of arteries).

These slice magnetic gradient $Gs_{tag}$, offset value $deltaF_{tag}$, and bandwidth $BW_{tag}$ are determined to meet the necessary and sufficient conditions of the ASTAR technique. In this embodiment, with the polarity of the offset value $deltaF_{tag}$ unchanged, the application polarity of the slice magnetic gradient Gs is changed. Alternatively, with the slice magnetic gradient Gs unchanged in polarity, the polarity of the offset value $deltaF_{tag}$ of the modulation frequency to an imaging slab may be changed (the absolute value of the offset value is unchanged), which can move the location of the offset to an opposite-directional position to a controlling slab described later.

Responsively to the application of the tagging IR pulse, the nuclear spins in the tagging slab are inverted once (i.e., tagged), then put into their T1 relaxation (spin-lattice relaxation) processes. The arteries tagged in the tagging slab inflow into the imaging slab under the T1 relaxation. As the imaging slab is excited off-resonance by the tagging IR pulse, the imaging slab has MT effects.

After the application of the tagging IR pulse, at the time when a desired inversion time TI elapsed, the first flip pulse P1 of which flip angle is set to a lower optimum value α is applied concurrently with a slice magnetic gradient Gs. The nuclear spins in the imaging slab are flipped by this application. This slice magnetic gradient Gs is then inverted in polarity for re-phasing the spins, with which a read-out magnetic gradient Gr is also applied in a certain direction. This read-out magnetic gradient Gr is then inverted in polarity for reading out an echo signal with frequency encoding, and its application lasts for an interval. For applying the first flip pulse, a phase-encoding magnetic gradient Ge=0 is realized.

After the application of the first flip pulse P1, as the time approaches an echo time TE that is an optimum, the first echo signal begins to grow in the imaging slab. This echo signal is detected by the RF coil 7, and then sent to the receiver 8R. In the receiver 8R, the echo signal is subjected to reception processing, such as amplification, conversion to an intermediate frequency, phase detection, and amplification in a baseband frequency, and then subjected to A/D conversion. Digital echo data is transferred to the calculator 10 via the sequencer 5, where echo data is mapped along a line at a position that corresponds to its phase-encoding amount in the k-space of an image. One preferred example of this mapping is "centric phase encoding" on which the echo data are acquired and mapped from lower frequencies starting at a phase-encoding of zero.

When the time comes at which the first acquisition of the echo signal should end, the application of the read-out magnetic gradient Gr is also ceased.

When a repetition time TR that is set to an optimum passes from the application of the first flip pulse P1, the second flip pulse P2 is applied with the slice magnetic gradient Gs. Responsively to the application of the second flip pulse P2, an echo signal is acquired in the same way as the above. The application of a series of flip pulses and the acquisition of echo signals are repetitively performed for each time of phase-encoding (for example, 128 times). For applying the second or later flip pulses, a phase-encoding magnetic gradient pulse Ge of which waveform area is altered in size for each time is applied before acquiring an echo signal. Additionally, to cancel the influence of the phase-encoding magnetic gradient pulse on spin phases, an opposite-polarity magnetic gradient Ge is applied after the completion of the echo signal acquisition.

Such a rewinding magnetic gradient may also be applied in the read-out and/or slice direction, if necessary.

As a result, the first one shot for the tagging scan allows the two-dimensional entire k-space to be mapped with echo data (raw data).

After waiting for an adequate recovery time $T_{recovery}$, for the recovery of spin states, the first one-shot scan in the controlling mode is launched.

In this scan, a pre-saturation pulse is first applied, like the above. Then, a slice magnetic gradient $Gs=Gs_{cont}$ and a controlling IR pulse (180° RF pulse: an offset value of its modulation frequency=$deltaF_{cont}$, its bandwidth=$BW_{cont}$) are applied. This slice magnetic gradient $Gs_{cont}(<GS_{tag})$, offset value $deltaF_{cont}(=deltaF_{tag}$: the absolute values thereof equal to each other), and bandwidth $BW_{cont}(= BW_{tag})$ are determined to satisfy the necessary and sufficient conditions for the ASTAR technique, as described before.

This enables, as shown in FIG. 1, a controlling slab to be selectively located over a wider thickness than the tagging slab, asymmetrically in position with the tagging slab in the controlling side to the imaging slab (parietal region side to the imaging slab; inflowing side of veins). That is, because the position offset amount $Offset_{cont}$ of the controlling slab is set to fully avoid the parietal region, the thickness $Thick_{cont}$ of the controlling slab becomes a proportionally large one (see FIG. 1).

Hence the nuclear spins in the controlling slab are inverted once, before proceeding to their T1 relaxation processes. However, this slab is located at a position almost separated from the parietal region, thereby causing no excitation of the nuclear spins in the veins of the parietal region (i.e., not tagged). Moreover, this causes an off-resonance excitation to the imaging slab, causing MT effects therein. The amount of the MT effects caused by the controlling scan is equal or substantially equal to that in the tagging scan stated above.

The reason is that the tagging and controlling IR pulses are based on the ASTAR technique. That is, with the offset frequencies of both the IR pulses to the imaging slab kept equal to each other, one distance between the imaging and tagging slabs and the other distance between the imaging and controlling slabs are controlled, as one scale factor (ratio) in thickness between the tagging and controlling slabs and the other scale factor (ratio) in positional offset between the tagging and controlling slabs are adjusted to the same value. That is, the reason is that the thickness of the controlling slab is set to a larger value proportional to its positional offset. Adequate control of the distances is able to realize a situation under which the control slab is not located or not substantially located on the veins in the head. The MT effects in the imaging slab caused by both the IR pulses can therefore be equal or substantially equal to each other, and only one-way blood blows can be tagged for detection.

After the application of the controlling IR pulse, at the time when the inversion time TI comes, echo acquisition from the imaging slab starts with n-pieces of flip pules on the FE technique, as described before, In compliance with the interleaved order, the first time of controlling scan is followed by the second time of tagging scan after the given recovery time $T_{recovery}$, which is performed in the same way as described already. After this tagging scan, there is again an interval defined by the given recovery time $T_{recovery}$, before the second time of controlling scan is performed in the same manner as above.

Hereinafter, similarly, the tagging and controlling scans are repetitively performed given times for averaging on the interleaved order.

The explanation will again return to FIG. 4. After the host computer 6 commands a scan at step 34 or 35, the sequencer 5 is responsible for detailed instructions that should be done for the scan. Thus after its command, the host computer 6 immediately sends to the calculator 10 other commands for various types of calculation (step 36). Responsively to this, the calculator 10 performs reading of acquired raw data, averaging, reconstruction, calculation of absolute values, calculation of differences (production of ASL image data), and others in an appropriate order and at appropriate timing.

Figure 7:
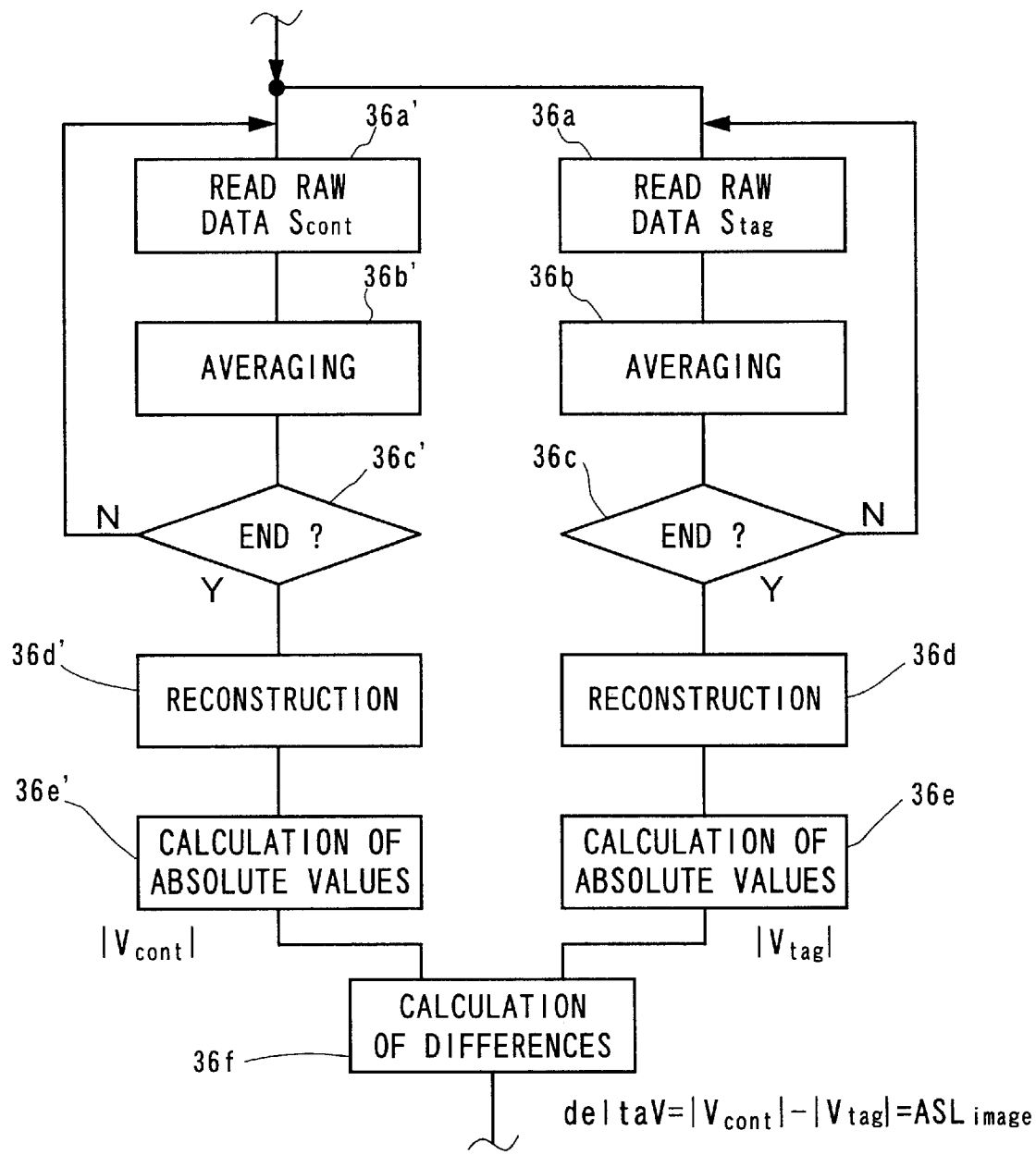
FIG. 7 is an outlined flowchart exemplifying procedures of processing performed by a calculator.
Figure 8:
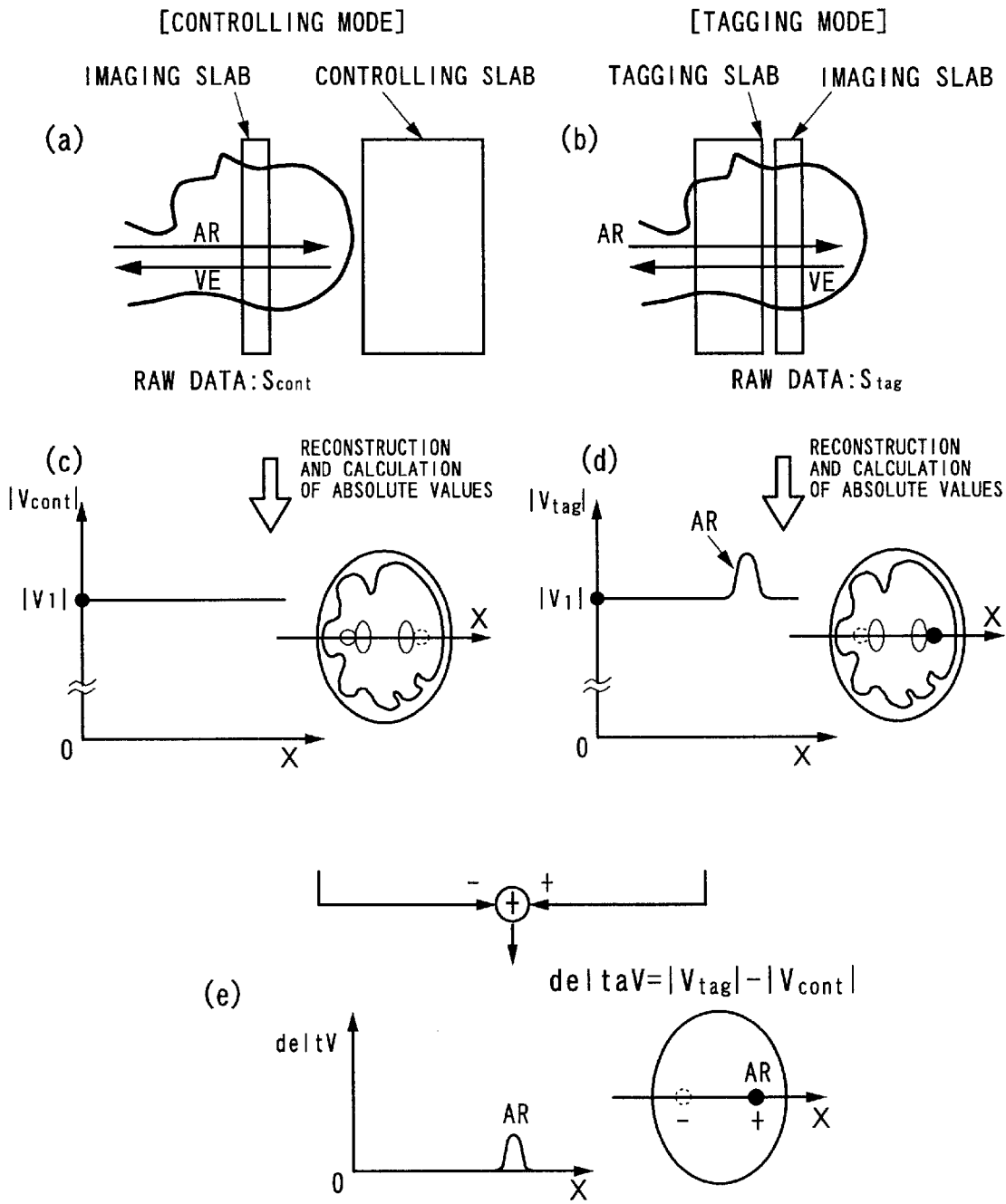
FIG. 8 is an illustration showing a flow of data processing performed after the acquisition of raw data.

One example of the processing performed by the calculator 10 is shown in FIGS. 7 and 8. FIG. 7 shows a conceptual flowchart of the processing and FIG. 8 pictorially illustrates data production associated with the processing. Incidentally, a flow of the processing in FIG. 7 is just one example, and the foregoing various kinds of calculation and processing can be performed in a variety of orders. Some examples for the modified orders will be shown in FIGS. 10 to 13.

In the processing flow in FIG. 7, the calculator 10 first reads data sent from the receiver 8R via the sequencer 5, that is, raw data $S_{tag}$ acquired with the tagging scan or raw data $S_{cont}$ acquired with the controlling scan (step 36a or 36a'). The raw data $S_{tag}$ and $S_{cont}$ are composed of complex data, respectively.

The raw data $S_{tag}$ and $S_{cont}$ are subject to averaging (for example, moving average) for improving an S/N (step 36b or 36b'). Both reading the raw data and averaging are carried out concurrently with scans and continued until the scan consisting of all the shots in each mode is completed (step 36c or 36c').

On completing all the averaging performed in this way, the calculator gains a set of averages of the raw data $S_{tag}$ on the tagging scan and another set of averages of the raw data $S_{cont}$ on the controlling scan, respectively. Then the calculator 10 reconstructs each of the raw data $S_{tag}$ and $S_{cont}$ into image data (step S36d or 36d'), before it calculates absolute values of each set of the raw data (step 36e and 36e'). Hence reconstructed image data $|V_{tag}|$ and $|V_{cont}|$ are produced.

The calculator 10 then calculates mutual differences between the image data $|V_{tag}|$ and $|V_{cont}|$ (step 36f). Namely, differences on:

$$\text{delta}V = |V_{cont}| - |V_{tag}|$$

are calculated pixel by pixel, and these difference values deltaV provide ASL image data $ASL_{image}$ in the real space.

After having obtained the final ASL image data, the host computer 6 sends out commands for both displaying and storing the image data to the calculator 10, memory unit 11 and display 12 (step 37). Hence an ASL image $ASL_{image}$ is visualized on the display 12.

According to the ASTAR technique thus-described, MT effects due to the controlling and tagging IR pulses are made to agree or almost agree to each other. Hence, as pictorially shown in FIG. 8, the signals from the tissue of both the image data $|V_{tag}|$ and $|V_{cont}|$ are nearly the same level in intensity (=|V1|). Additionally, an arterial flow AR inflowing from the tagging side is tagged by the tagging slab, thus the signal intensity $|V_{tag}|$ at the blood flow being raised (refer to FIG. 8(d)). On one hand, owing to the fact that the controlling slab is located so as to be separated in position from the parietal region, a venous flow VE inflowing into the imaging slab from the controlling side is never or scarcely tagged, thus the signal intensity $|V_{cont}|$ at the vein is approximately identical to that in the tissue (refer to FIG. 8(c)).

Accordingly, performing mutual difference between the image data $|V_{tag}|$ and $|V_{cont}|$ causes the signals in the tissue to canceled completely or almost completely, so that there steadily remain the signals at pixels residing on only the artery AR tagged by the tagging IR pulse (refer to FIG. 8(e)).

With no particular increase in the SAR or RF, the MT effects due to the tagging and controlling IR pulses are surely canceled, and difference errors inherent in tissue's blood flow in producing ASL image are reduced. Additionally, blood flowing from the tagging side (for example, arteries) is imaged solely, whilst blood that flows from the controlling side (for example, veins) is suppressed in data acquisition. Thus assigning an artery inflow side to the tagging side is able to non-invasively provide an MRA image consisting of only the signal components of arterial flows, with higher accuracy and quality (only objective blood flows are imaged in a higher S/N) and a simplified operation (which is almost similar to the conventional one).

Incidentally, for a perfusion image, a lower limit $\text{delta}V_{high}$ for distinguishing large blood vessels to be suppressed, for instance, arteries AR, is set in the processing by the calculator 10. The foregoing differences deltaV are subject to the operation of a threshold on the above-mentioned expression (r):

$$\text{delta}V = (\text{delta}V < \text{delta}V_{high})$$

Figure 9:
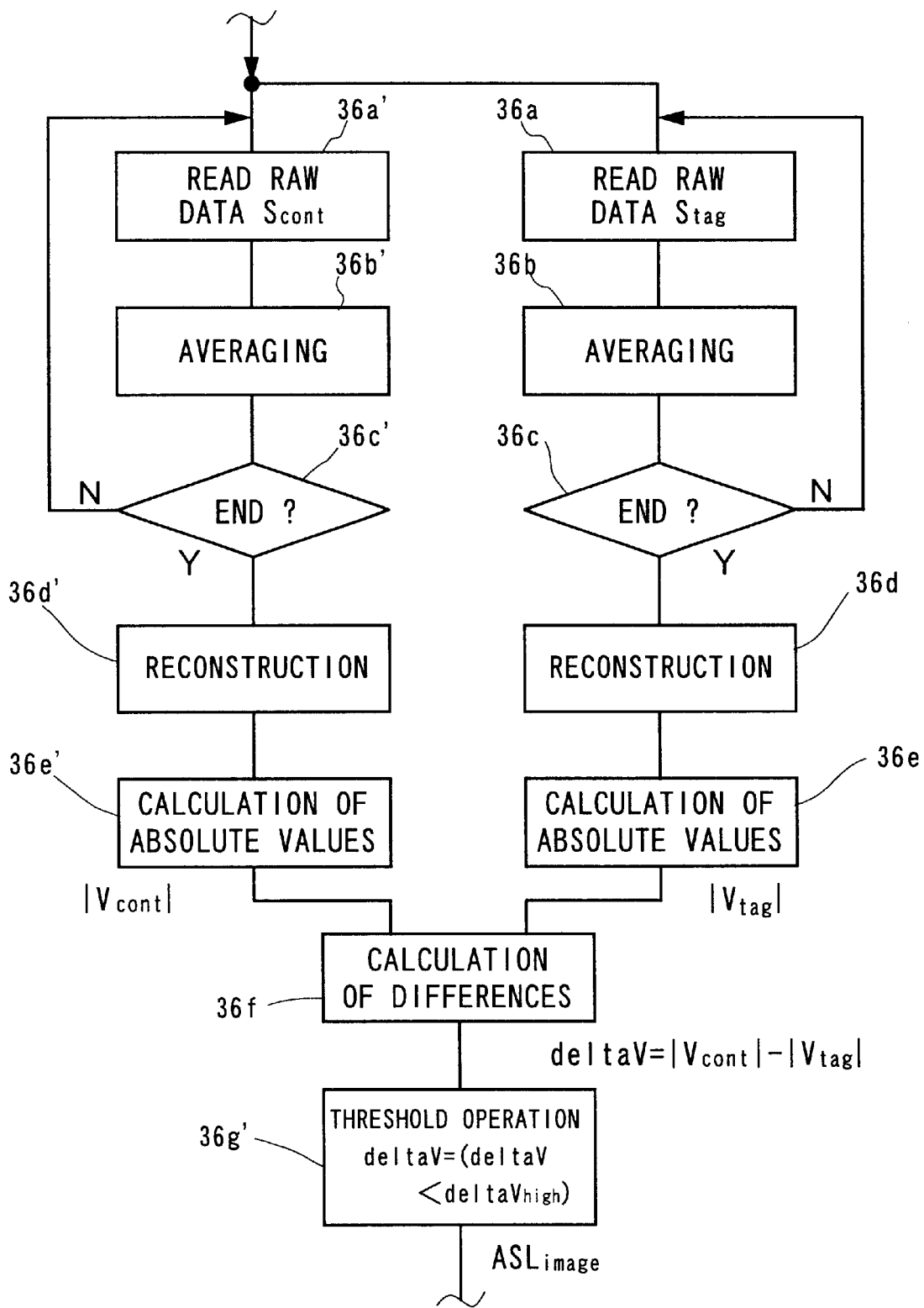
FIG. 9 is an outlined flowchart exemplifying procedures of processing for perfusion images performed by the calculator.
Figure 10:
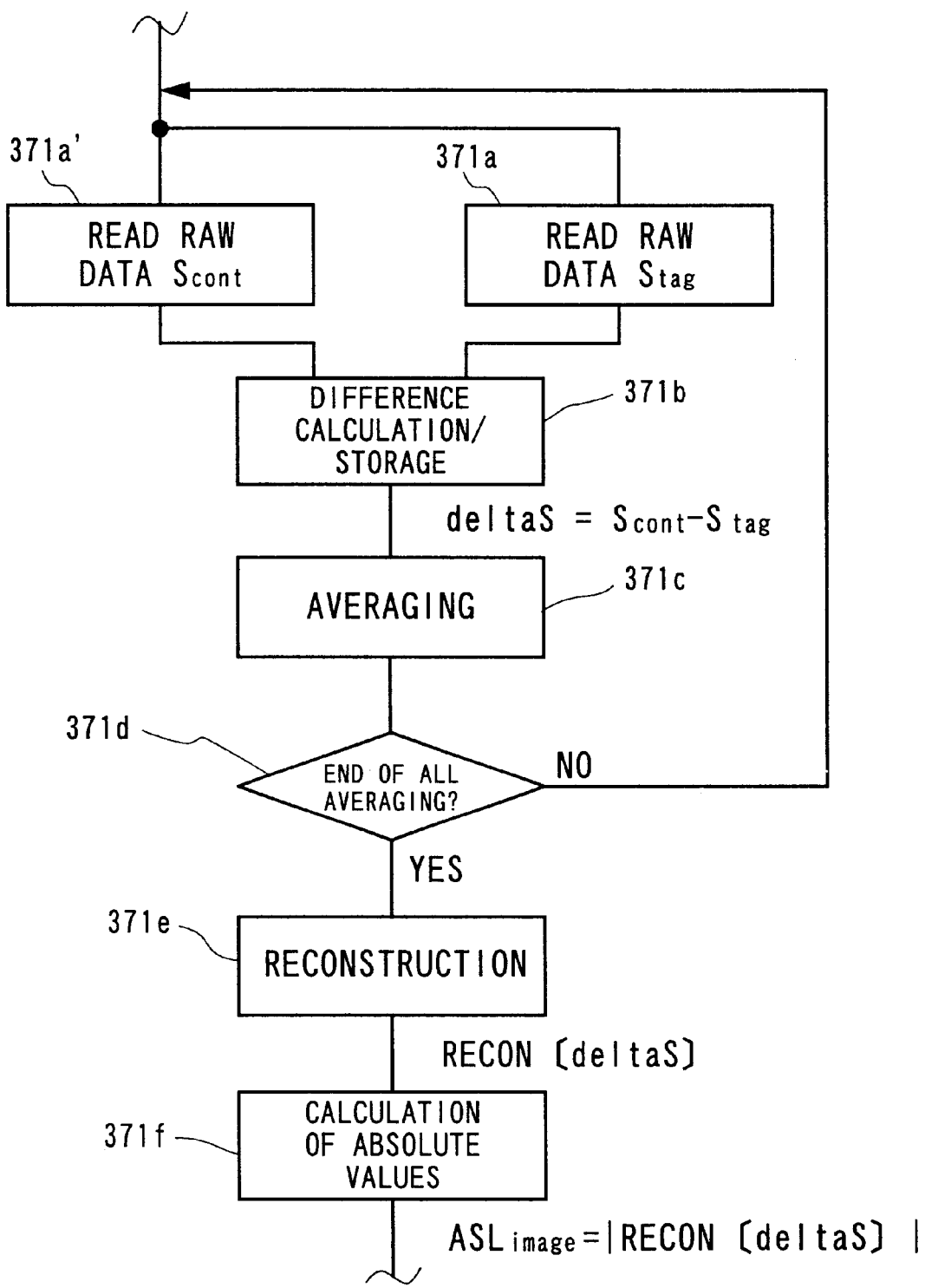
FIG. 10 is an outlined flowchart showing another example of procedures of processing performed by the calculator.

One example of such processing is shown in FIG. 9, in which the threshold operation (step 36g') is conducted after the difference calculation at step 36f.

This provides a perfusion image in which the signals from large blood vessels (such as arteries) are suppressed. In consequence, besides the advantages in imaging the MRA images, perfusion images of only blood in tissue, which excludes large blood vessels generally considered unnecessary, can be provided in a steady manner, and such an image can be increased in terms of clinical significance.

In both of the tagging and controlling scans in this embodiment, because the pre-saturation pulse is applied, the spins in stationary tissue are previously saturated. Thus it is possible to improve accuracy in performing ASL difference of signals induced from tissue, which can provide ASL images of higher quality. As another example, the application of the pre-saturation pulse may be omitted.

Moreover, because the interleaved order is employed as the scan order in the tagging and controlling scans, the relaxation time of the spins in both of the tagging and controlling slabs can be shortened.

The present inventor conducted both of experimental imaging of a phantom and imaging (MRA image and perfusion image) of the human head, and confirmed in either imaging that the ASTAR technique is effective.

FIGS. 10 to 13 show other examples of the order of processing performed by the calculator 10. In the order of processing in FIG. 10, differences are calculated in the stage of raw data $|S_{cont}|$ and $|S_{tag}|$, which is followed by addition (averaging) (steps 371a, 371a', 371b to 371d). These processes are conducted in parallel with the scans. The raw data that underwent the difference calculation and averaging are reconstructed, before those absolute values are calculated (steps 371e and 371f). This order of processing simplifies the processing and reduces an amount of necessary calculation.

Figure 11:
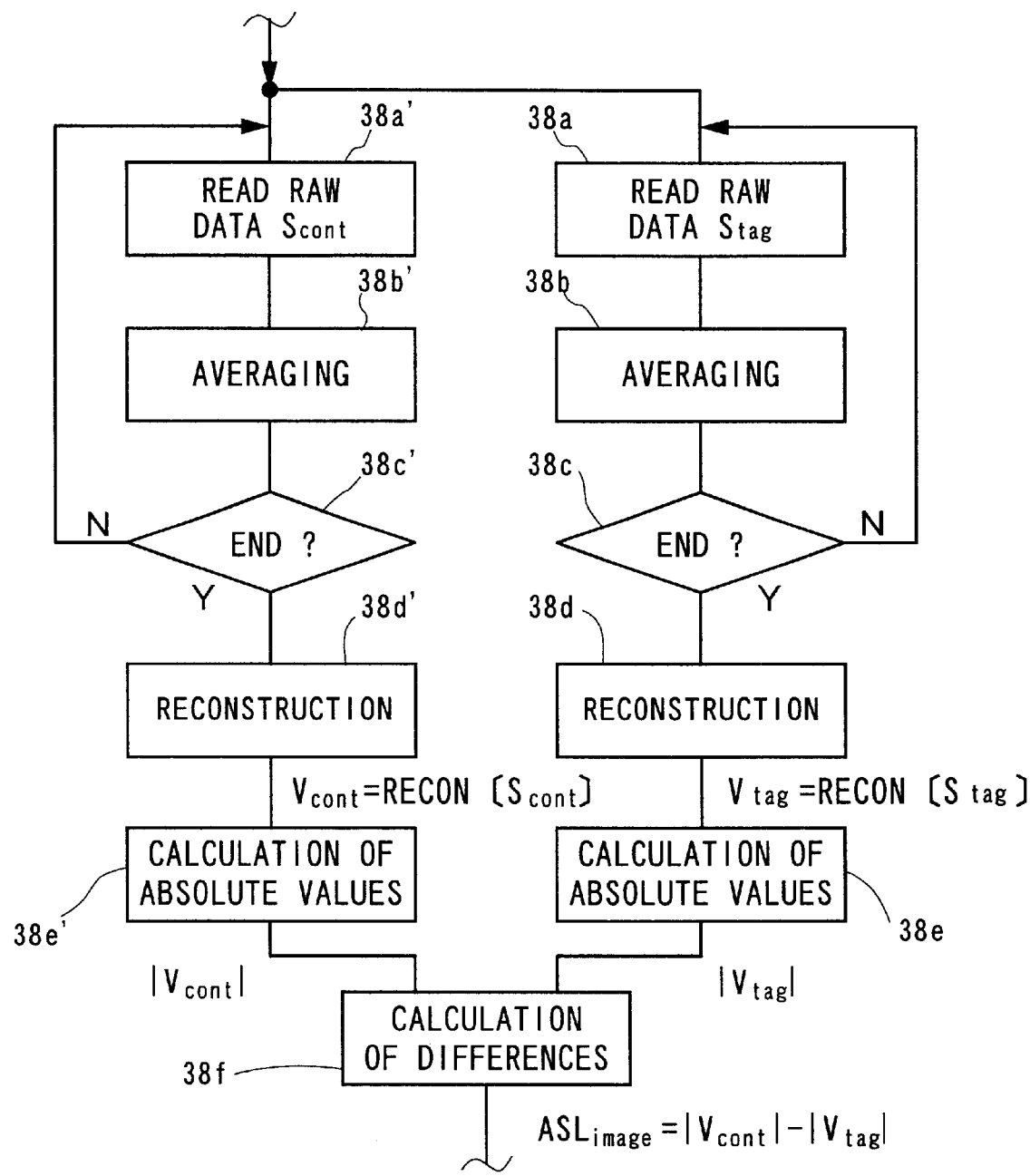
FIG. 11 is an outlined flowchart showing still another example of procedures of processing performed by the calculator.

According to the order of processing in FIG. 11, in the stage of raw data $S_{cont}$ and $S_{tag}$) averaging, reconstruction, and calculation of absolute values are conducted in this order for each set of the raw data (steps 38a to 38e, 38a' to 38e'). Then, differences between the reconstructed image data are calculated to obtain an ASL image $ASL_{image}$ (step 38f). In this order of processing, the calculation of absolute values is followed by the difference calculation. Noise components can therefore be reduced. Moreover, because the images of the absolute values produced in the processing can be memorized, the background (tissue) of an ASL image can be eliminated by post-correction, even if the background remains in the ASL image.

Figure 12:
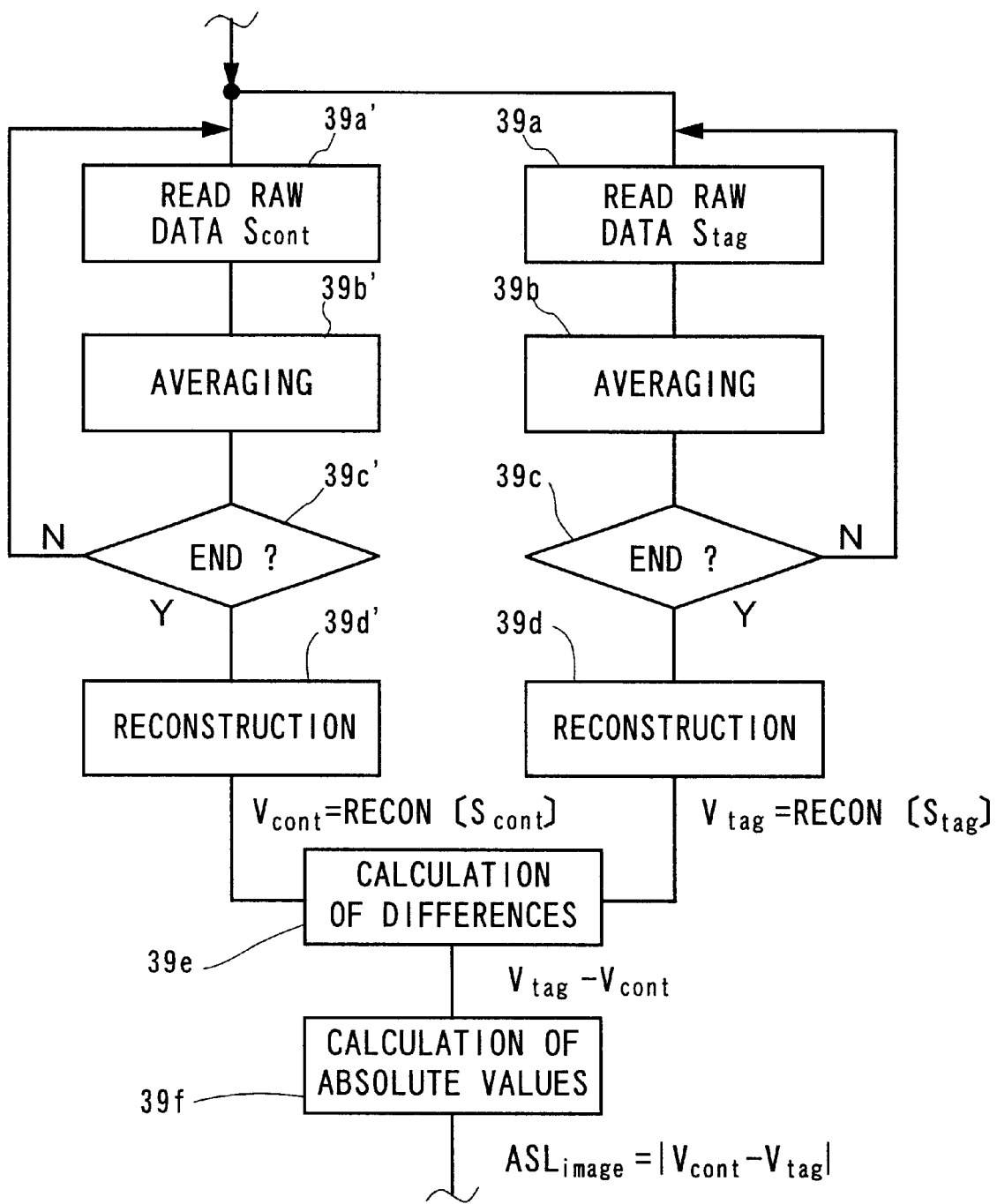
FIG. 12 is an outlined flowchart showing still another example of procedures of processing performed by the calculator.

The order of processing shown in FIG. 12 includes the same steps ranging down to reconstruction as those in FIG. 11. After the reconstruction, difference calculation is done first (steps 39a to 39d, 39a' to 39d', and 39e). Absolute values are then calculated to obtain an ASL image $ASL_{image}$ (step 39f). This order is able to provide ASL images with relatively simplified processing.

Figure 13:
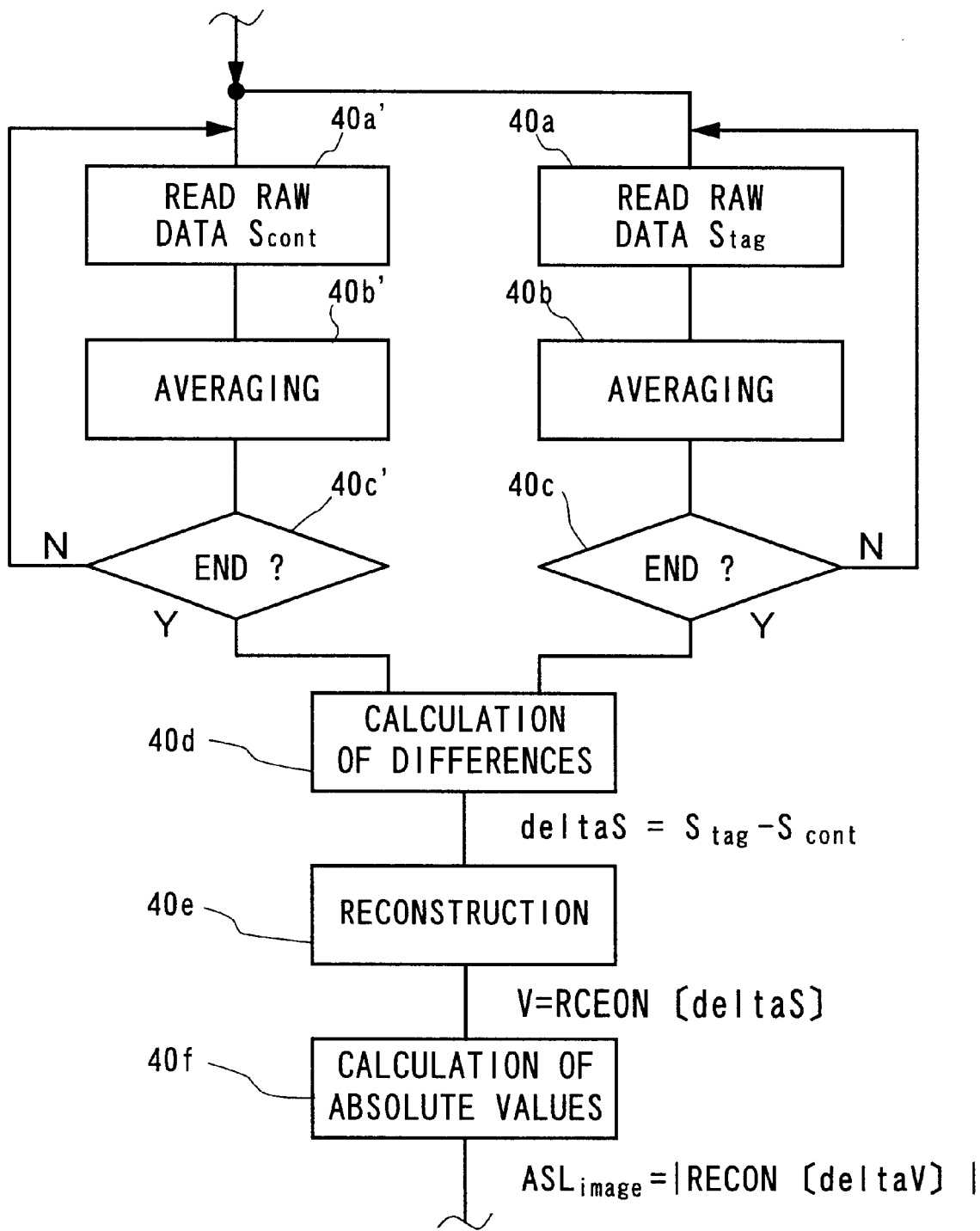
FIG. 13 is an outlined flowchart showing still another example of procedures of processing performed by the calculator.

In the order of processing in FIG. 13, averaging is performed on raw (steps 40a to 40c and 40a' to 40c'). After this, differences are calculated immediately to produce an ASL image, each of real and imaginary data of the differences is reconstructed, and those absolute values is calculated to obtain ASL image data (steps 40d to 40f). This is also capable of supplying ASL images with relatively simple processing.

(Second Embodiment)

Referring to FIGS. 14 to 17, a second embodiment of the present invention will now be described. In this embodiment, identical or similar constituents to those in the first embodiment use the same references, so that the explanation for those are omitted or simplified.

Figure 2:
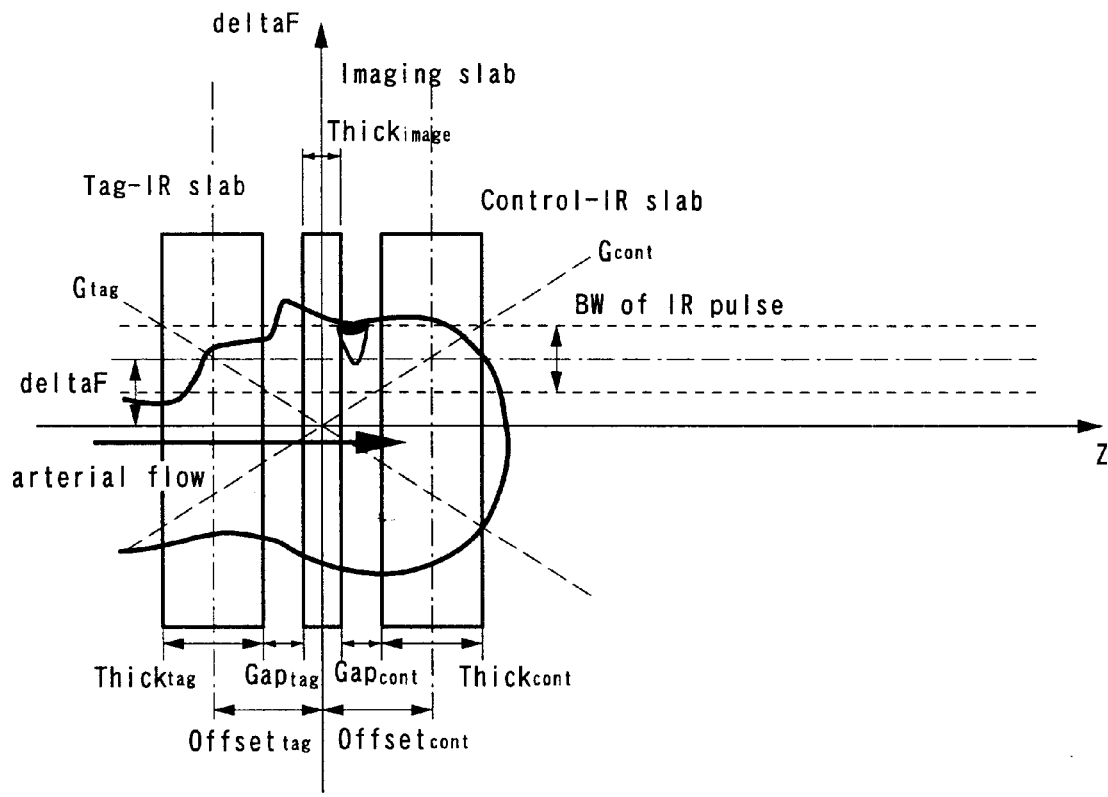
FIG. 2 shows the principle of an EPISTAR technique according to another mode of the present invention.

An MRI system of this embodiment performs MRA imaging or perfusion imaging on the basis of the EPISTAR technique that is the other approach of the present invention. The EPISTAR technique itself has been explained with FIG. 2.

Figure 14:
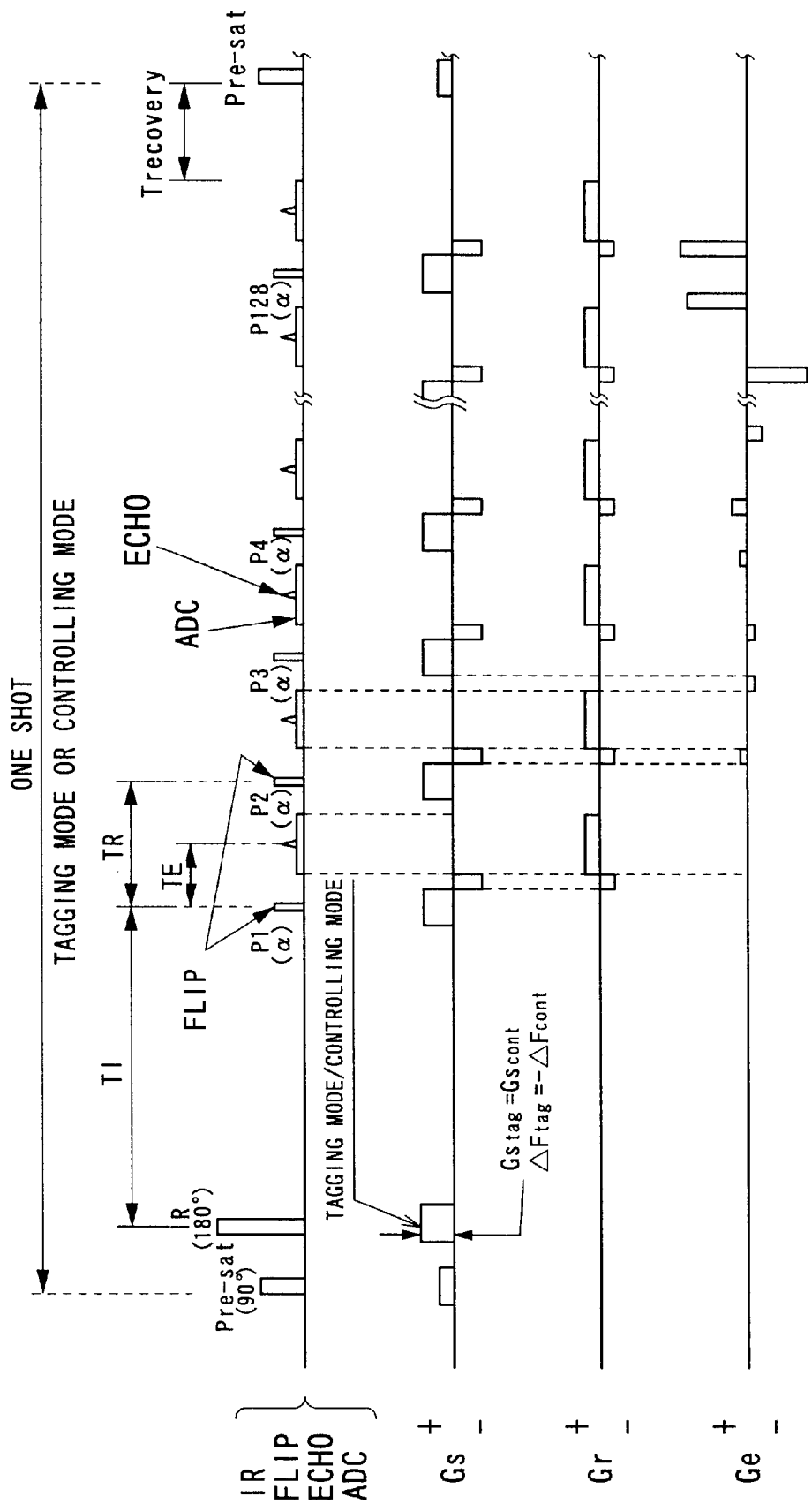
FIG. 14 is a timing chart of a pulse sequence executed at each shot on the basis of an EPISTAR technique according to a second embodiment of the present invention (, which explains both of the tagging and controlling scans)

Like the first embodiment, the host computer 6 issues a command to the sequencer 5, in which the command provides, as a T1-enhanced pulse sequence, a fast FE pulse sequence with an IR pulse, as shown in FIG. 14, which is performed, for example, an interleaved order. As to tagging and controlling IR pulses used in this pulse sequence, their bandwidths BW equal to each other ($BW_{tag}=BW_{cont}$) and their offset frequencies deltaF equal in absolute values to each other, though their polarities are opposite to each other ($deltaF_{tag}=-deltaF_{cont}$). With this condition, gradients Gs of the same intensity ($GS_{tag}=Gs_{cont}$) are used.

Data acquisition is conducted with an identical or similar manner as in the first embodiment under the control of the sequencer 5. Raw data $S_{tag}$ and $S_{cont}$, each of which is composed of complex data, are acquired in each of tagging and controlling modes, then sent to the calculator 10 in which they experience processing to produce images exemplified in FIG. 15. A series of processes shown therein feature a threshold operation. The raw data $S_{tag}$ and $S_{cont}$ are each read, averaged, reconstructed into images, and calculated into absolute values, before being subject to the calculation of differences between those data, so that ASL image data $deltaV=|V_{tag}|-|V_{cont}|$ are obtained (steps 41a to 41e, 41a' to 41e', and 41f. Then, a threshold operation is conducted so as to satisfy the expression (v), that is, $$deltaV>0$$

Figure 16:
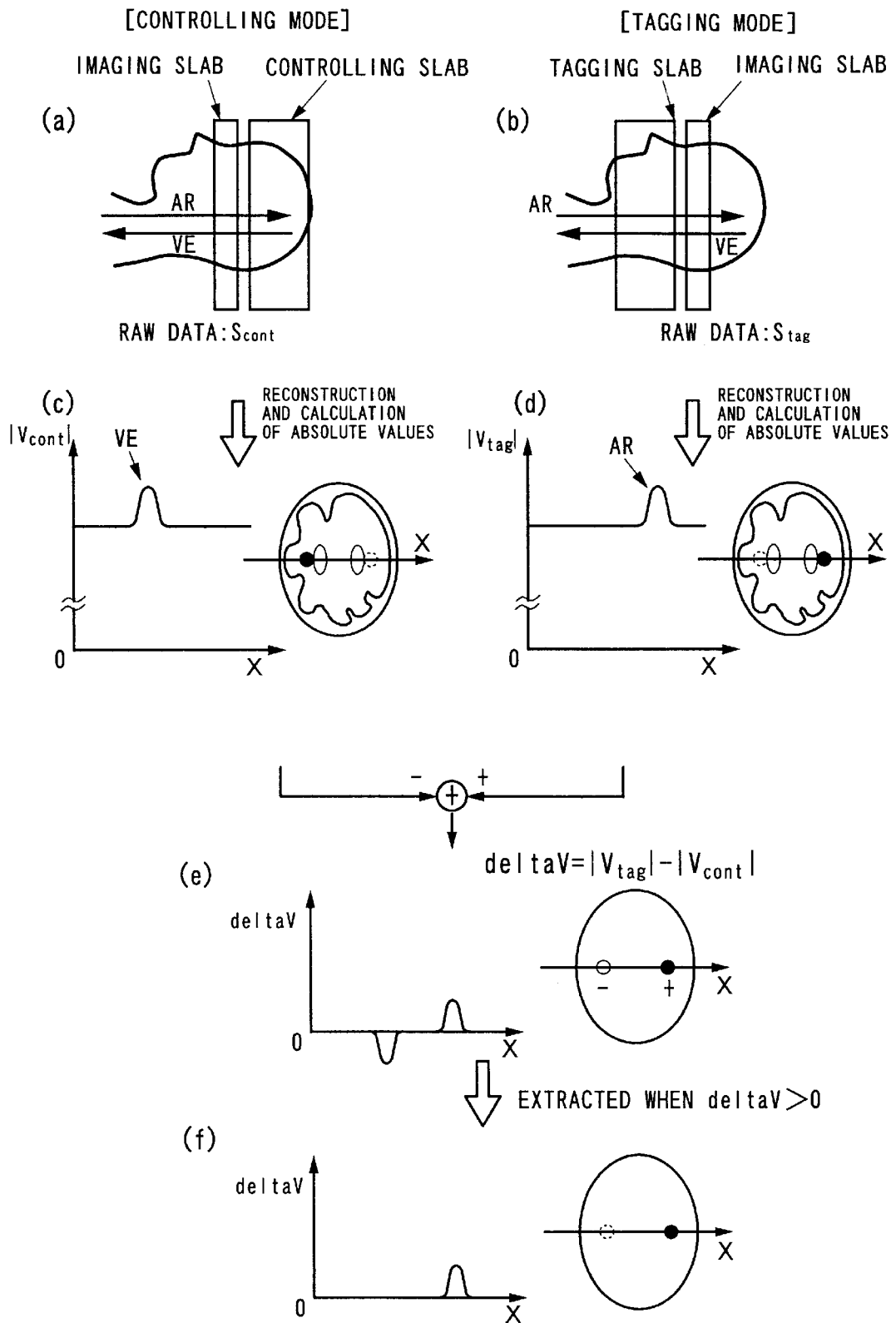
FIG. 16 is an illustration showing a flow of data processing performed after the acquisition of raw data in the second embodiment.

(refer to step 41f and FIG. 16 (e) and (f)). An ASL image consisting of ASL image data satisfying deltaV>0 can therefore be obtained.

This ASL image undergoes the threshold operation, thus providing a blood vessel image in which a vein VE is eliminated but only an artery AR is expressed. FIG. 16 pictorially shows processing for obtaining such an image.

Figure 15:
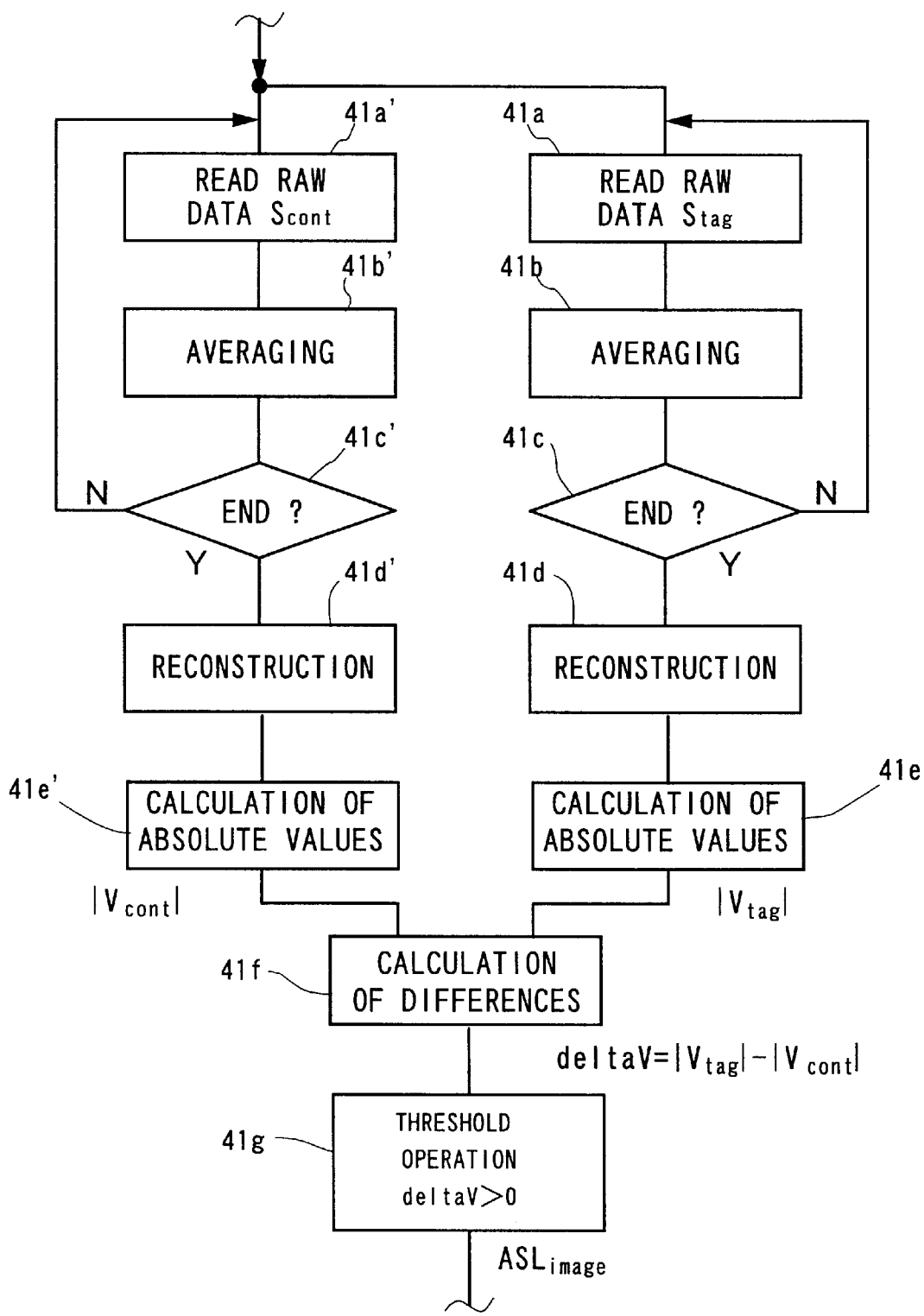
FIG. 15 outlines a flowchart showing one example of procedures of processing for imaging ASL images, which is executed by the calculator in a second embodiment.
Figure 17:
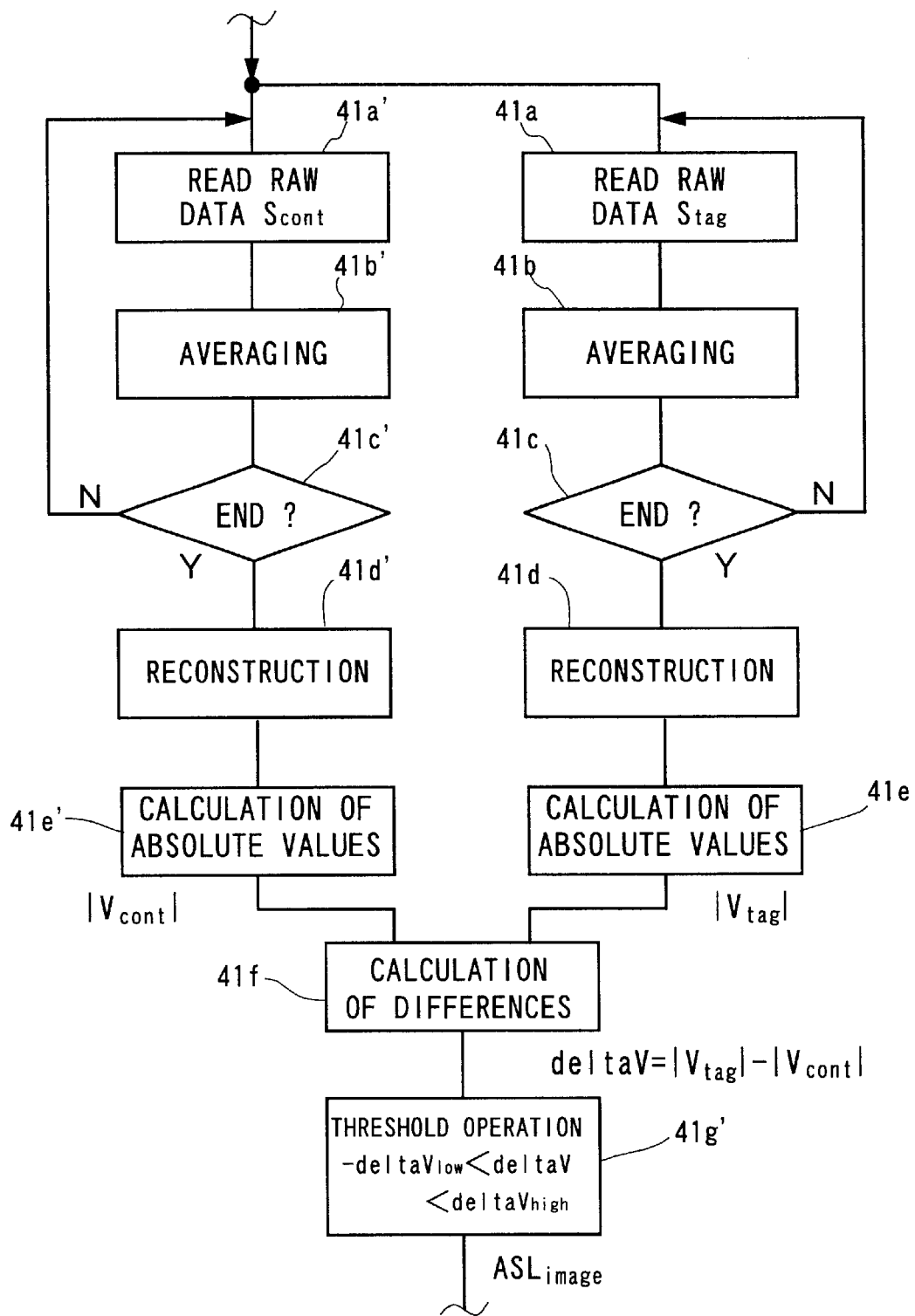
FIG. 17 is an outlined flowchart exemplifying procedures of processing for imaging perfusion images, which is executed by the calculator in the second embodiment.

Incidentally, for imaging perfusion based on the EPISTAR technique, the processing can be shown in FIG. 17, where a threshold operation on the expression (w) is conducted at step 41g' that corresponds to step 41g in FIG. 15.

The first and second embodiments exemplify the employment of a pulse sequence in which a single inversion pulse is used to acquire all echo data for one image. Instead, a pulse sequence that includes a plurality of inversion pulses to acquire all echo data for one image, i.e., a segmented fast FE sequence, can be employed.

Moreover, although the first and second embodiments show the MRI system and MR imaging method for executing a fast FE sequence including an IR pulse, pulse sequences applicable to the present invention are not confined to such a sequence. Any pulse sequence can be used, as long as an IR pulse (180° RF pulse) or saturation pulse (90° RF pulse) is used to cause the T1 relaxation process, during which time raw data fulfilling the k-space can be acquired. For example, in the case of a fast SE sequence with an IR pulse, though a single flip pulse and a plurality of refocusing pulses are applied to acquire data fulfilling the k-space, the flip angles of both of the flip and refocusing pulses can be adjusted to appropriate values. These flip angles enable a signal decay due to T2 attenuation to be suppressed, thus being able to produce a condition under which both of the T1 relaxation and the T2 attenuation are balanced with each other. Therefore, this pulse sequence is also usable for the present invention.

Moreover, the first and second embodiments exemplify the human head as a region to be imaged, but this region may be selected from various other objects, such as the ren, liver, or muscle blood flow.

Further, in the first and second embodiments, exemplified is setting the tagging and controlling slabs parallel with the imaging slab through each IR pulse. However the present invention is not restricted to this configuration; for example, the tagging, imaging, and controlling slabs may be located in a mutual orthogonal or oblique positional relationship.

Still further, the first and second embodiments exemplify the performance of two-dimensional scanning, but three-dimensional scanning can be practiced as well.

(Third Embodiment)

Figure 18:
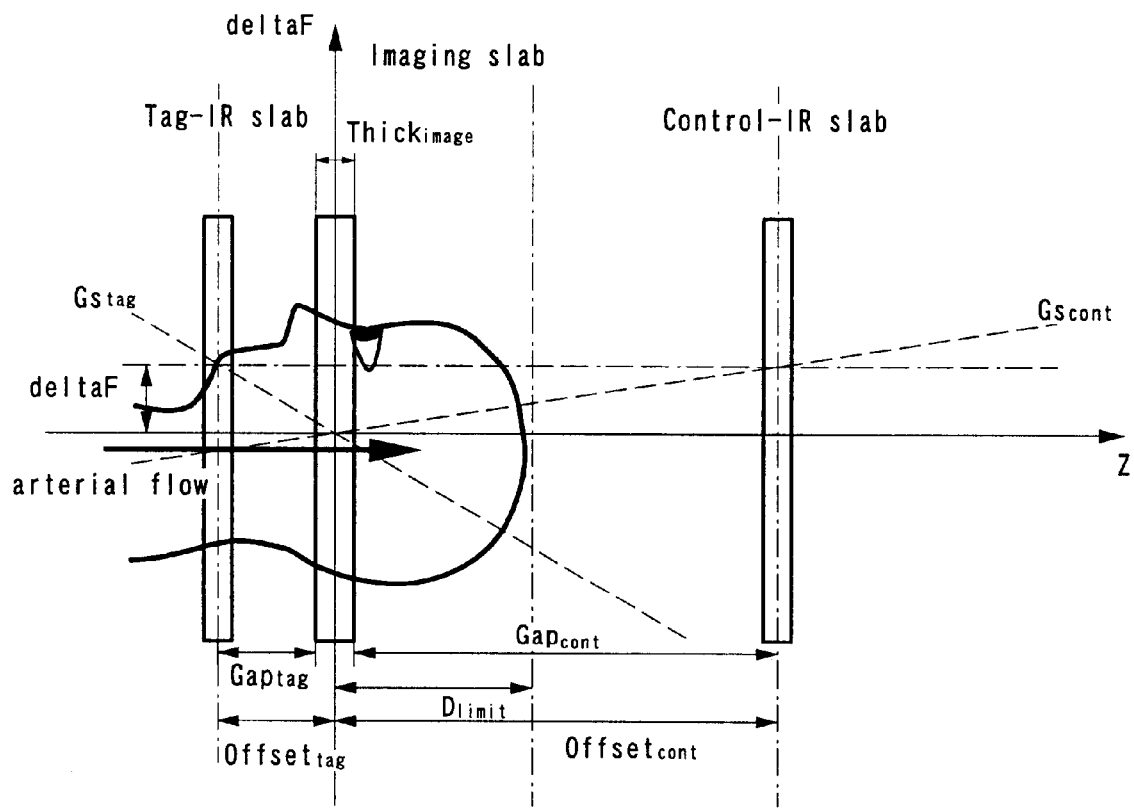
FIG. 18 illustrates the principle of an ASTAR technique (based on the CASL techniques) according to a third embodiment that corresponds to another mode of the present invention.
Figure 19:
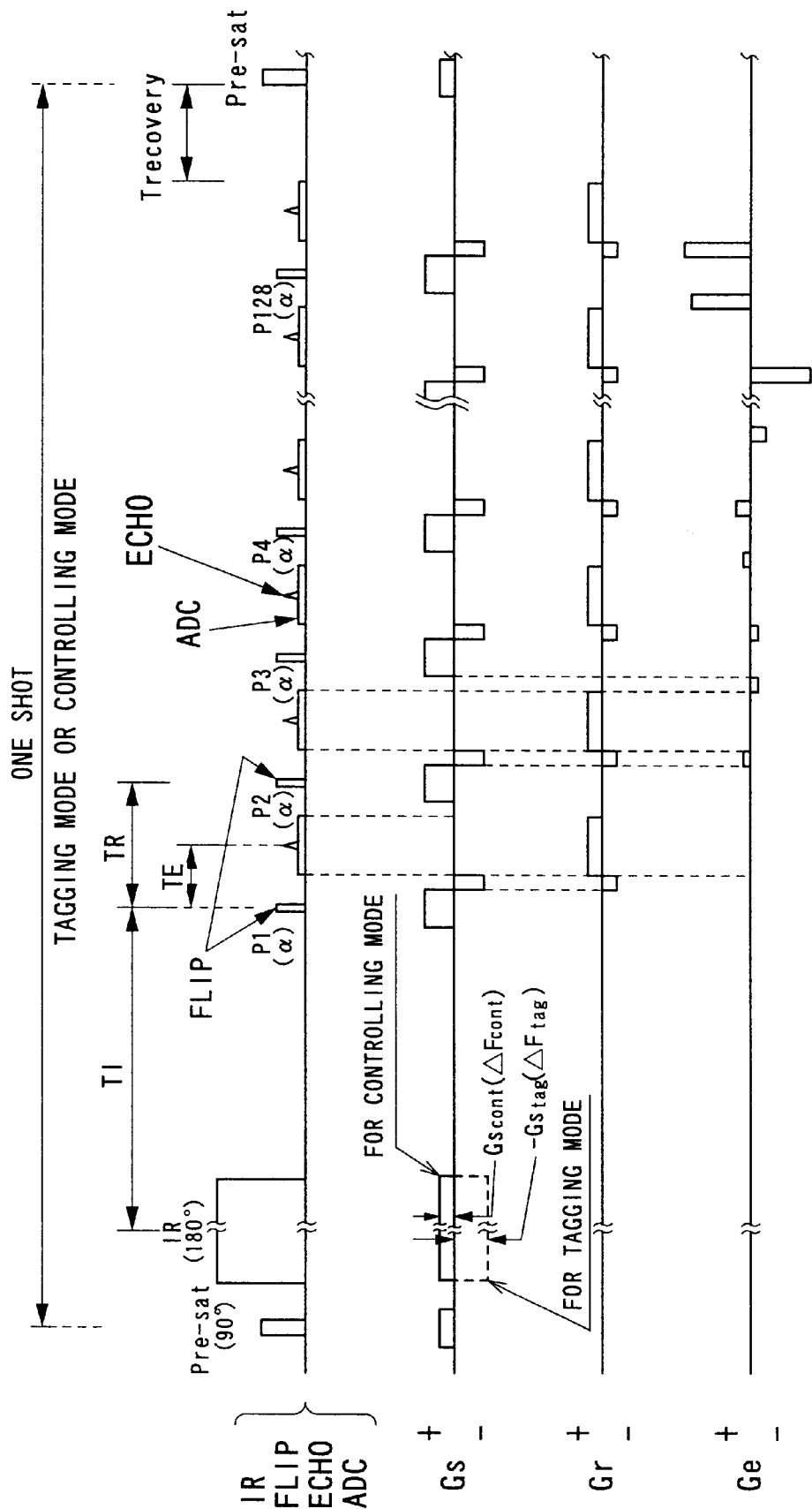
FIG. 19 exemplifies a pulse sequence usable in the third embodiment.

Referring to FIGS. 18 and 19, a third embodiment of the present invention will now be explained.

The present embodiment is concerned with an MRI system that conducts the ASTAR technique described in the first embodiment, based on the CASL technique. The hardware configuration of the system is identical to that in the previous embodiments, while the procedures of ASL imaging are similar to the ASTAR (based on the PASL technique) described in the first embodiment.

FIG. 18 illustrates a relationship between the spatial positions of slabs (slices) and gradients for imaging on the ASTAR (based on the CASL technique) according to this embodiment. FIG. 19 depicts one example of a practical pulse sequence.

As illustrated in FIG. 18, IR pulses to be applied in tagging and controlling modes meet an adiabatic condition of a certain magnitude and consists of a continuous wave of a single frequency, which are applied for a period beyond a certain time (for example, a sine wave of a single frequency is applied for 1 to 3 sec. or thereabout).

The RF coil for applying such a continuous wave is formed by a head-dedicated coil ordinarily used. Thus, as shown in FIG. 18, a slice magnetic gradient $Gs_{tag}$ for tagging is such determined that a tagging slab (slice) is located on an artery portion positioned in the blood inflow side, for instance, to an imaging slab. A slice magnetic gradient $Gs_{cont}$ for controlling, on one hand, is such determined that a controlling slab (slice) is located in separation from the parietal region in the body axis (Z-axis) direction, as shown therein.

Additionally, an offset frequency deltaF is adjusted so as to meet a condition of:

$$deltaF=Gs_{tag} \cdot Offset_{tag}$$

$$=Gs_{cont} \cdot Offset_{cont}.$$

When an excitation frequency at the slice-directional center of the imaging slab is $F_0$, the slice-directional centers of the tagging and controlling slabs (slices) are excited by:

$$single\ frequency=F_0+(deltaF).$$

Thus, in the tagging mode, as shown in FIG. 18, an artery portion at a blood inflow region to the imaging slab, for example, is tagged by the tagging slab (slice). As shown therein as well, in the controlling mode, a position in the space separated from the parietal region in the body-axial (Z-axial) direction is excited by the controlling slab (slice). Due to the fact that the tagging IR pulse is formed into a continuous pulse, the tagging slab becomes a greatly thin slice (theoretically, a plate) and is perpendicular to, for example, an artery. This allows the spins in blood to be inverted, then, as they are, to flow downstream, so that they inflow into the imaging slab. Since the controlling IR pulse is formed by a continuous pulse, the controlling slab also becomes a greatly thin slice (theoretically, a plate).

A train of imaging pulses in the pulse sequence shown in FIG. 19 and data processing of ASL imaging after the acquisition of echo data are similar to those in the first embodiment, and an ASL image is obtained based on differences between tagging and controlling images.

Therefore, most of the MT effects caused at the position corresponding to the excitation frequency $F_0$, i.e., the slice-directional center of the imaging slab, are canceled by the difference calculation because amounts of those emerging in both of the tagging and controlling modes are almost the same. There is obtained a highly fine ASL image, from which the influence of the MT effects is substantially excluded.

Further, an advantage thanks to the characteristic of the CASL technique is obtained as well. That is, using the tagging and controlling IR pulses each consisting of a continuous wave permits an excited slab (slice) to become a plate as thin as possible. As a result, unlike the condition under which, as seen in the PASL technique, spins of blood which are excited at a portion within the tagging slab, which is far from the imaging slab, inflow into the imaging slice with a large delay time, those excited in the tagging slab (slice) on the CASL technique are able to inflow into the imaging slab with less delay time. Particularly, making the tagging slab (slice) closer to the imaging slab as possible as could is able to reduce the delay time, correspondingly. Since the T1 relaxation of the spins of blood that inflowed into the imaging slab does not advance so far, the SNR of a blood signal from the imaging slab is improved more than that in the PASL technique.

In this embodiment, instead of the ordinary head-dedicated RF coil employed as the RF coil, a small transmitting RF coil to be located with no sensitivity on an imaging slab may be used. In this case, a gradient is not applied and the transmitting RF coil is located such that its sensitivity region covers, for example, an artery inflowing into the imaging slab. This is able to tag an objective blood that inflows into the imaging slab.

(Fourth Embodiment)

Referring to FIGS. 20 to 23, a fourth embodiment of the present invention will now be described.

The present embodiment is directed to a technique used in the ASL imaging, which is reducing errors in difference inherent in stationary tissue (the errors are the results of difference, in which the differences are ideally zero). This error-reducing technique can be applied to a wide variety of ASL imaging methods including the ASTAR, FAIR, EPISTAR, independently of the type of its pulse, i.e., the PASL or CASL technique.

Hereinafter, one example of the technique of reducing errors in difference will now be described with respect to the ASTAR on the PASL technique.

Errors in difference are briefly described. As described in the foregoing embodiments, in the ASL imaging having the tagging and controlling modes, tagging and controlling images are obtained with amounts of MT effects of stationary tissue in an imaging slab being the same with each other, and undergo a mutual difference operation to provide an image of blood signals.

However, this ASL imaging requires that, after the tagging, scanning have to wait for a period (T1 time) during which a large-vessel arterial flow defuses into the tissue. Hence, generally, the signals from stationary tissue is approximately 100 to 1000 times larger than signals from blood flow. If there is instability of the RF system, body motions of a patient, or the like, signals from stationary tissue (i.e., errors in difference) that cannot be ignored might be left after calculating differences.

In this embodiment, an object is added that prevents such difference errors steadily in order to provide ASL imaging capable of finely depicting blood flows in a desired direction.

Figure 20:
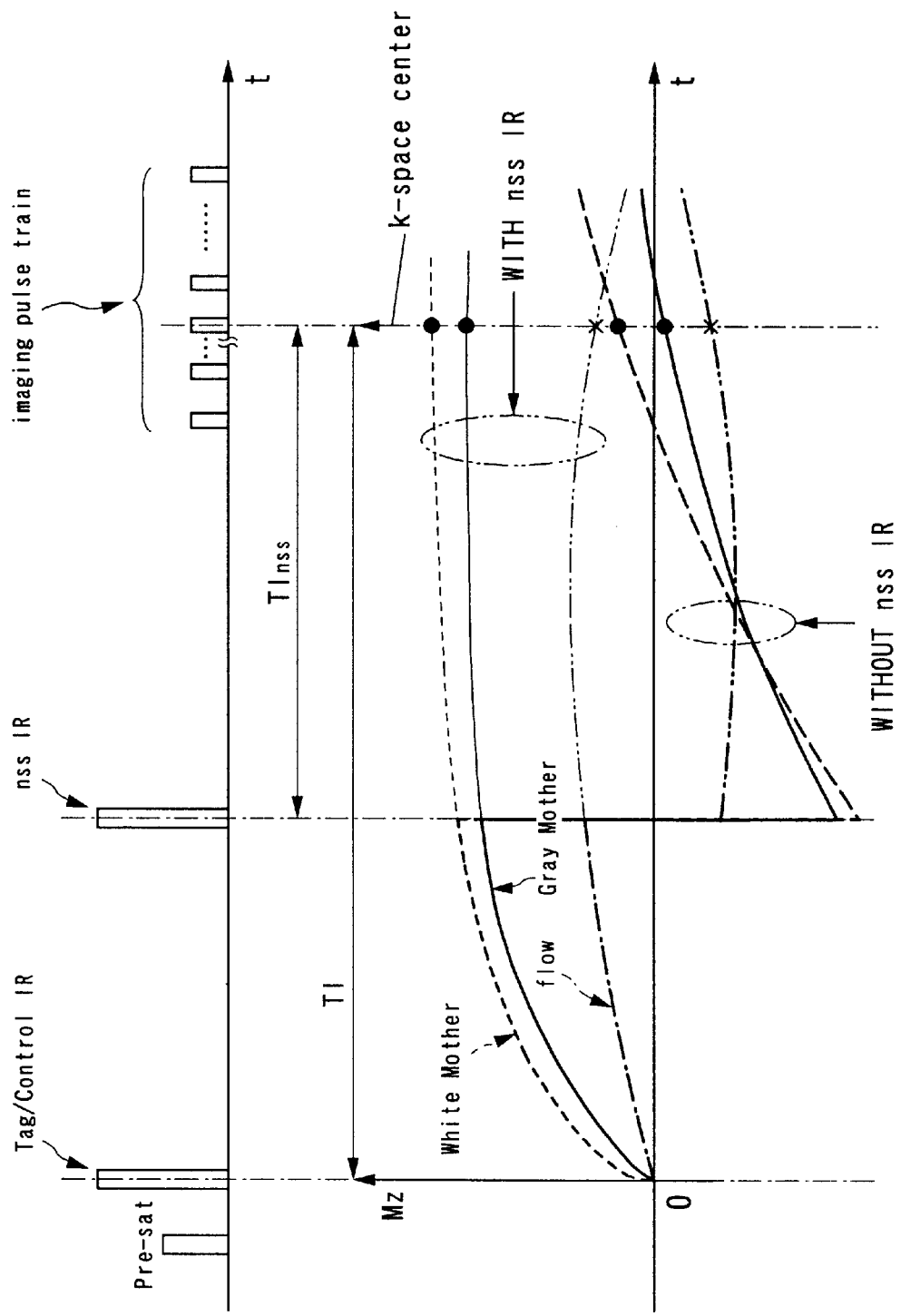
FIG. 20 is an outlined pulse sequence of the ASTAR technique (based on the PASL technique) that uses a non-slice selective IR pulse, which is according to a fourth embodiment of the present invention.

A pulse sequence of this embodiment, which is on the ASTAR based on the PASL technique, is shown in FIG. 20. This pulse sequence is carried out for obtaining an ASL image in the identical procedures and processing to those in the first embodiment.

Figure 21:
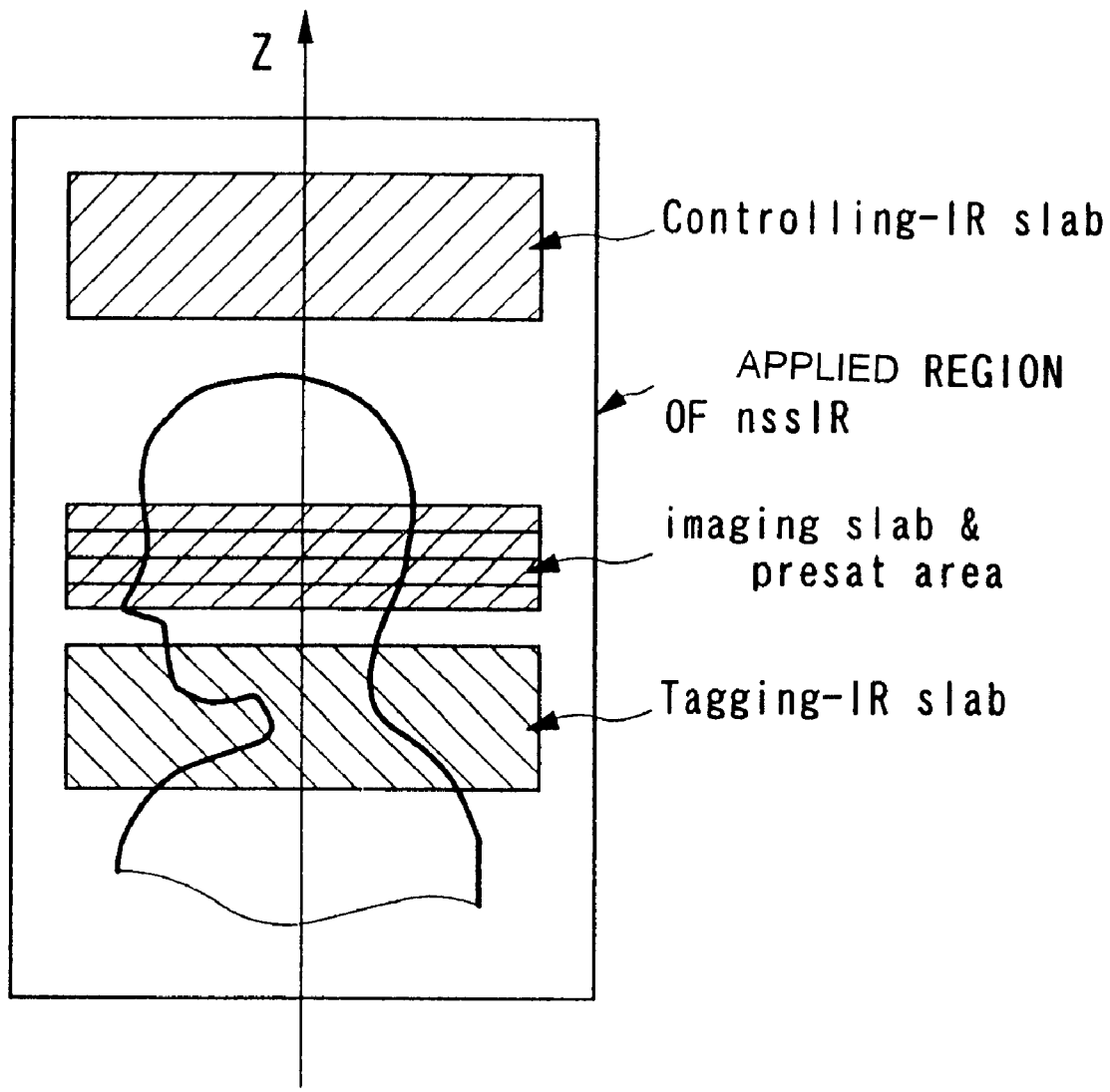
FIG. 21 is an illustration explaining the positional relationship between a non-selective region and slabs in the fourth embodiment.

As shown therein, between an application time of a tagging/controlling IR pulse and a time in the train of imaging pulses, which corresponds to the phase-encoding center of the k-space, a pulse referred to as a non-slice selective IR pulse (nssIR pulse) is applied once with no application of a slice magnetic gradient. This nssIR pulse is non-selectively applied, but it is enough for an actual case that this pulse is applied to a region of a thickness over a slab thickness containing tagging and imaging slabs, as shown in FIG. 21. Incidentally, in the case of FIG. 20, the nssIR pulse is applied one time, but it may be applied two or more times.

The nssIR pulse is characteristic of suppressing the generation of difference errors of signals from stationary tissue.

In an objective imaging slab, there exists stationary tissue having different T1 values, for example, if stated from a shorter T1 value, fat, white matter (WM), gray matter (GM), and CSF. Of these, major stationary tissue constituents in the brain parenchyma are WM and GM. Hence, the time $TI_{cont}$ (see FIG. 20) from the application of the nssIR pulse to an acquisition time of data mapped in the center of the k-space is set to an amount that enables the longitudinal magnetization Mz of GM and WM to become approximately zero on average. The larger the number of nssIR pulses to be applied, the smaller the differences in the longitudinal magnetization Mz owing to differences in TI time of various types of stationary tissue.

According to an experiment the present inventor conducted, it was confirmed that, when TI=1000 to 1500 ms and $TI_{nss}$=300 to 400 ms, the signals from GM and WM can be lowered down to 1/10 or less, compared to those obtained with no application of the nssIR pulse.

Though an optimum $TI_{nss}$ time is changed to some degree depending on the TI time (the longer TI, the longer $TI_{nss}$) the changes with respect to GM and WM are about 100 msec. The $TI_{nss}$ time can therefore be considered a constant.

As to spins of blood in an imaging slab, both of the spins that have inflowed therein before and immediately after the application of the nssIR pulse are inverted without distinctions. Likewise, the spins are also inverted by both of the tagging and controlling IR pulses. The results of differences between the tagging and controlling modes become a state under which only the polarities are inverted but magnitudes are almost the same as those acquired without the nssIR pulse if the spins are fully inverted by the nssIR pulse.

Figure 22:
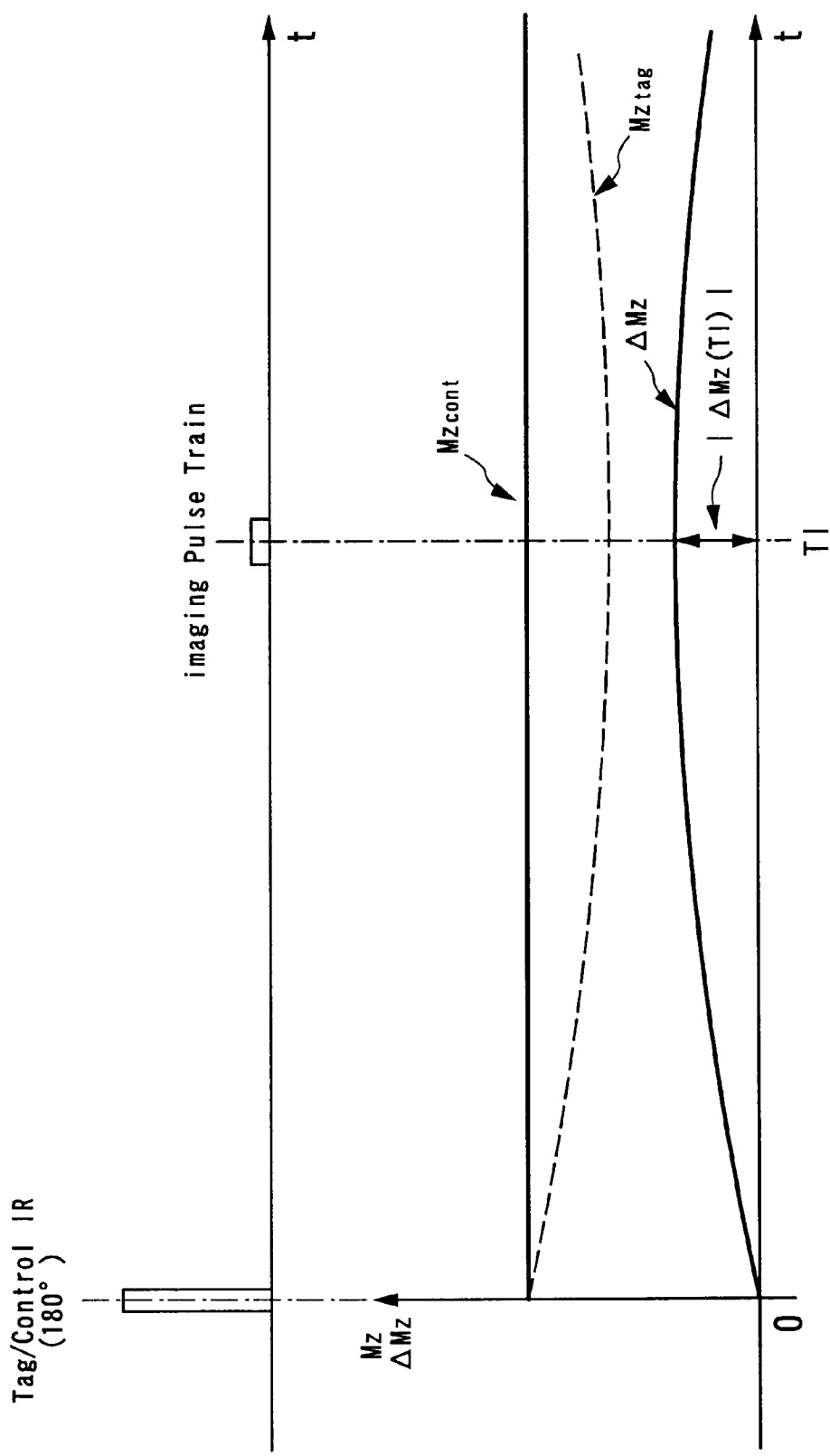
FIG. 22 explains changes in the longitudinal magnetization of a flow component acquired when the non-slice selective IR pulse is not used.
Figure 23:
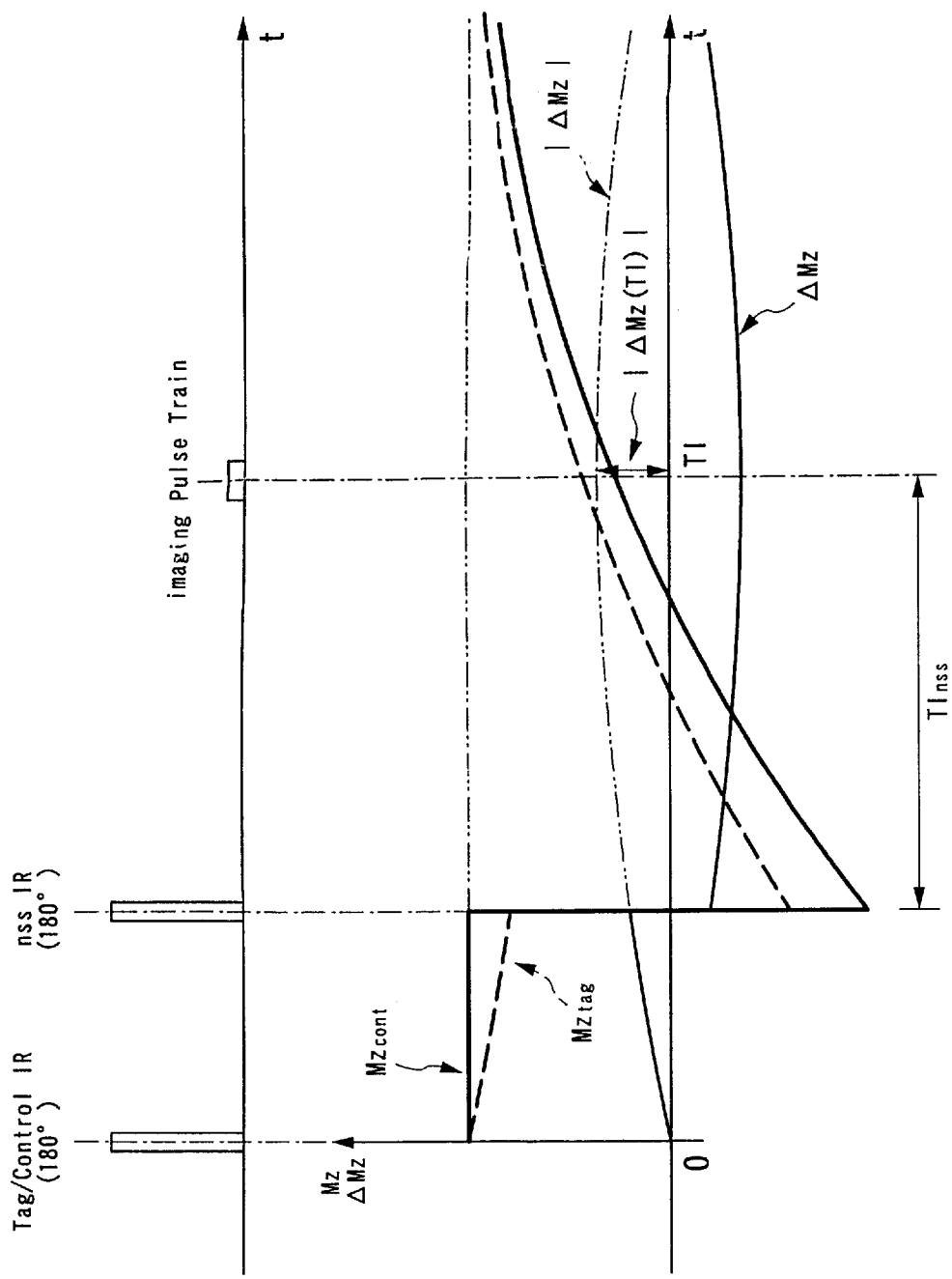
FIG. 23 explains changes in the longitudinal magnetization of a flow component acquired when the non-slice selective IR pulse is used.

FIGS. 22 and 23 show temporal changes in the longitudinal magnetization Mz of only blood flow on the ASTAR technique, where water is exemplified with and without the nssIR pulse in each of the controlling and tagging modes. As can be seen, if all the spins of a blood component in tagging and imaging regions are steadily inverted by the application of the nssIR pulse, their differences $\Delta Mz = \Delta Mz_{cont} - \Delta Mz_{tag}$ result in only the inverted signs, but their magnitudes are not changed. The pixel values of an image are calculated in absolute values, so that it is understood that they become the same as those obtained without the nssIR pulse.

In this way, the nssIR pulse is used and the time $TI_{nss}$ from the application of the nssIR pulse to an acquisition time of data to be mapped in the center of the k-space is set that the longitudinal magnetization Mz remaining in major constituents of stationary tissue become nearly zero on average. Thus, differences (difference errors) for stationary tissue, which are conducted between tagging and controlling images, become almost zero. Even when there is instability of the RF system in the imaging system, or body motions of a patient in scanning, signals from stationary tissue are suppressed, resulting in that only blood flowing in a desired direction can be depicted in a steadier manner.

In the ASL imaging, a ratio of signals from blood or flow to that from stationary tissue is less in intensity by a quantity of one to two digit, compared to the ordinary MRA. Therefore, as described in this embodiment, reducing the intensity of signals from the stationary tissue as possible as could, difference errors inherent in stationary tissue can be reduced. The depiction performance of blood flow can be noticeably increased.

The present invention is not restricted to the foregoing embodiments that are just representatives. A person in the art may deform or alter them into various other modes without departing from the gist of the present invention, on the basis of the contents written in the accompanying claims.

According to the foregoing MRI system and MR imaging method, ASL imaging is performed on the PASL or CASL technique. Compared to the conventional (the conventional NEW-EPISTAR technique), the ASL imaging is carried out so that SAR and RF power are not particularly increased. The tagging and controlling scans permit MT effects caused in an imaging slab to be canceled with each other in a stable and accurate manner, thus reducing differences in signal intensities from stationary tissue of the imaging slab. Additionally, signal components from blood inflowing from the controlling slab side can surely be suppressed and signal components from blood inflowing from the tagging slab side are imaged alone. For example, this is able to provide an image in which only arterial flows are depicted. Thus, two inconsistent needs for ASL imaging are met simultaneously.

Particularly, using a non-slice selective IR pulse can further reduce difference errors specific to stationary tissue, providing highly finer ASL images.

As a result, perfusion images or MRA images of higher accuracy and quality can steadily be obtained with a relatively simplified manner and burdens on a patient are relieved thanks to non-invasiveness.

What we claim is:

1. An MRI system for obtaining an ASL (Arterial Spin Labeling) image of an imaging slab of a subject placed in a static magnetic field by locating a tagging slab and a controlling slab on both sides of the imaging slab, respectively, the system comprising:

storing means for storing information indicative of a first pulse sequence including a first RF pulse and a first magnetic gradient both for selective-exciting the tagging slab and for storing information indicative of a second pulse sequence including a second RF pulse and a second magnetic gradient both for selective-exciting the tagging slab controlling slab, in which offset amounts of exciting central frequencies of both the first and second RF pulses to a central position of the imaging slab are equal to each other and offset positions of both the tagging slab and the controlling slab to the imaging slab are different from each other;

first scanning means for performing toward the subject the first pulse sequence so as to acquire a first MR signal from the imaging slab;

second scanning means for performing toward the subject the second pulse sequence so as to acquire a second MR signal from the imaging slab; and image producing means for producing the ASL image based on a difference between the first and second MR signals.

2. The system of claim 1, wherein each of the first and second RF pulses consists of a single-frequency continuous RF pulse determined correspondingly to each of the first and second magnetic gradients so as to allow each of the tagging and controlling slabs to be excited at a desired slab position.

3. The system of claim 2 wherein the storing means stores the information concerning the first and second RF pulses and the first and second magnetic gradients determined such that a ratio between thicknesses of the tagging and controlling slabs and a further ratio between the positional offsets of the tagging and controlling slabs to the imaging slab are equal to each other.

4. The system of claim 3, wherein each of the first and second RF pulses is a pulsed RF pulse having a certain frequency band.

5. The system of claim 1, wherein each of the first and second RF pulses is an IR (inversion recovery) pulse inverting spins of the subject, and each of the first and second scanning means is configured to apply the IR pulse in mutually opposite polarities to the imaging slab during the performance of each of the first and second pulse sequences.

6. The system of claim 5, wherein the imaging slab is located at a head portion of the subject, and the storing means includes means for setting the controlling slab spatially separately from the head portion.

7. The system of claim 1, wherein the image producing means includes mans for extracting from the difference of the MR signals a signal component of not more than a threshold determined as a minimum signal intensity for a blood vessel to be suppressed of the subject.

8. The MRI system of claim 1, wherein the first and second pulse sequences are the same type of pulse sequence enhancing a longitudinal magnetization of spins of the subject.

9. The MRI system of claim 8, wherein each of the first and second RF pulses is an IR (inversion recovery) pulse for inverting the spins, the IR pulse being applied slice-selectively to each of the tagging and controlling slabs.

10. The MRI system of claim 8, wherein each of the first and second pulse sequences includes a pre-saturation pulse for previously saturating the spins of the subject.

11. The MRI system of claim 1, wherein the first and second scanning means are configured to perform the first and second pulse sequences in an interleaved order along which the first and second pulse sequences are repeated by turns.

12. The MRI system of claim 1, wherein each of the first and second scanning means is configured to perform each of the first and second pulse sequences a plurality of times so that the MR signal is acquired the plurality of times from the imaging slab, and the image producing means includes means for averaging the MR signals acquired over the plurality of times.

13. The MRI system of claim 3, wherein the storing means comprises providing means for providing, as known amounts, a slab thickness of the imaging slab, a slab thickness of the tagging slab, a distance between the imaging and tagging slabs, and a distance between the imaging and controlling slabs; and calculating means for calculating the slab thickness and the positional offset amount of the controlling slab on the basis of the known amounts.

14. An MRI system comprising:

a first scanning means for applying a first RF wave to a tagging slab to be located in one side of an imaging slab of a subject so as to acquire a first MR signal from the imaging slab;

a second scanning means for applying a second RF wave to a controlling slab to be located, symmetrically to the tagging slab, in the other side of the imaging slab so as to acquire a second MR signal from the imaging slab; and image data producing means for producing image data on the basis of the first and second MR signals, wherein the image data producing means comprise a first and second absolute-value calculating means for calculating absolute values of the first and second MR signals after reconstruction thereof, respectively;

difference means for performing mutual differences between the absolute values of the first and second MR signals; and extracting means for extracting image data of a desired signal component from differences obtained by the difference means.

15. The MRI system of claim 14, wherein the extracting means is configured to apply to the differences threshold processing with either a threshold determined to suppress the MR signal of a large-diameter blood vessel inflowing from a controlling slab side into the imaging slab and to extract image data indicative of a blood flow inflowing from a tagging slab side into the imaging slab or a further threshold determined to suppress the MR signal of a large-diameter blood vessel inflowing into the imaging slab and to extract image data indicative of perfusion inflowing into the imaging slab.

16. The MRI system of claim 1, wherein each of the first and second pulse sequences includes a non-slice selective IR pulse following application of the RF pulse as well as being applied to a region of the subject including the imaging slab, tagging slab, and controlling slab and an imaging pulse train following application of the non-slice selective IR pulse.

17. The MRI system of claim 16, wherein an interval between the application of the non-slice selective IR pulse and the application of the imaging pulse train in each of the first and second pulse sequences is determined so that a spin-lattice relaxation time of stationary tissue contained in the imaging slab becomes an amount to be regarded as being approximately zero on average when the imaging pulse train is applied.

18. The MRI system of claim 16, wherein the non-slice selective IR pulse consists of a plurality of non-slice selective IR pulses.

19. An MR imaging method of obtaining an ASL (Arterial Spin Labeling) image of an imaging slab of an subject placed in a static magnetic field by locating a tagging slab and a controlling slab on both sides of the imaging slab, respectively, the method comprising the steps of:

reading out information indicative of first and second pulse sequences set and stored in memory means, the first pulse sequence including a first RF pulse and a first magnetic gradient both for selective-exciting the tagging slab and the second pulse sequence including a second RF pulse and a second magnetic gradient both for selective-exciting the controlling slab, in which offset amounts of exciting central frequencies of both the first and second RF pulses to a central position of the imaging slab are equal to each other and offset positions of both the tagging slab and the controlling slab to the imaging slab are different from each other;

performing toward the subject both the first and second pulse sequences so as to acquire first and second MR signals from the imaging slab, respectively;

producing the ASL image based on a difference between the first and second MR signals.

20. An MRI system for obtaining an ASL (Arterial Spin Labeling) image of an imaging slab of an subject placed in a static magnetic field by locating a tagging slab and a controlling slab on both sides of the imaging slab, respectively, the system comprising:

storing means for storing information indicative of a first pulse sequence including a first RF pulse and a first magnetic gradient both for selective-exciting the tagging slab and for storing information indicative of a second pulse sequence including a second RF pulse and a second magnetic gradient both for selective-exciting the controlling slab, wherein (i) offset amounts of exciting central frequencies of both the first and second RF pulses to a central position of the imaging slab are equal to each other, (ii) offset positions of both the tagging slab and the controlling slab to the imaging slab are different from each other, and (iii) a ratio between thicknesses of the tagging and controlling slabs and a further ratio between the positional offsets of the tagging and controlling slabs to the imaging slab are equal to each other;

first scanning means for performing toward the subject the first pulse sequence so as to acquire a first MR signal from the imaging slab;

second scanning means for performing toward the subject the second pulse so as to acquire a second MR signal from the imaging slab; and image producing means for producing the ASL image based on a difference between the first and second MR signals.

21. The system of claim 20, wherein each of the first and second RF pulses is a pulsed RE pulse having a certain frequency band.

22. The MRI system of claim 20, wherein the storing means comprises providing means for providing, as known amounts, a slab thickness of the imaging slab, a slab thickness of the tagging slab, a distance between the imaging and tagging slabs, and a distance between the imaging and controlling slabs; and calculating means for calculating the slab thickness and the positional offset amount of the controlling slab on the basis of the known amounts.

* * * * *